(12) United States Patent
Moholkar

(10) Patent No.: US 10,582,918 B2
(45) Date of Patent: Mar. 10, 2020

(54) ASSEMBLIES FOR USE IN KNEE REPLACEMENT SURGERY

(71) Applicant: Kirti Moholkar, Barnt Green (GB)

(72) Inventor: Kirti Moholkar, Barnt Green (GB)

(*) Notice: Subject to any disclaimer, the term of this patent is extended or adjusted under 35 U.S.C. 154(b) by 890 days.

(21) Appl. No.: 14/893,207

(22) PCT Filed: May 21, 2014

(86) PCT No.: PCT/GB2014/051553
§ 371 (c)(1),
(2) Date: Nov. 23, 2015

(87) PCT Pub. No.: WO2014/188184
PCT Pub. Date: Nov. 27, 2014

(65) Prior Publication Data
US 2016/0106409 A1    Apr. 21, 2016

(30) Foreign Application Priority Data

May 23, 2013   (GB) .................................. 1309303.4
Jun. 3, 2013    (GB) .................................. 1309830.6
Jun. 11, 2013   (GB) .................................. 1310403.9

(51) Int. Cl.
A61B 17/02   (2006.01)
A61B 17/15   (2006.01)
A61B 5/107   (2006.01)
A61B 5/00    (2006.01)
(Continued)

(52) U.S. Cl.
CPC .......... *A61B 17/025* (2013.01); *A61B 5/1072* (2013.01); *A61B 5/4533* (2013.01); *A61B 5/4585* (2013.01); *A61B 5/4851* (2013.01); *A61B 17/155* (2013.01); *A61B 90/06* (2016.02); *A61B 17/157* (2013.01); *A61B 17/1764* (2013.01); *A61B 2017/0268* (2013.01); *A61B 2090/061* (2016.02); *A61B 2090/064* (2016.02); *A61B 2090/067* (2016.02)

(58) Field of Classification Search
CPC ..... A61B 17/025; A61B 17/15; A61B 17/154; A61B 17/155; A61B 17/157; A61B 2017/0268
See application file for complete search history.

(56) References Cited

U.S. PATENT DOCUMENTS 4,566,448 A * 1/1986 Rohr, Jr. .............. A61B 17/155
606/88
5,540,696 A * 7/1996 Booth, Jr. ............ A61B 17/025
606/102
(Continued)

FOREIGN PATENT DOCUMENTS

DE    102005049851 A1    4/2007
EP        1348382 A2    10/2003
(Continued)

*Primary Examiner* — Eric S Gibson
(74) *Attorney, Agent, or Firm* — Hodgson Russ LLP

(57) ABSTRACT

An assembly (10) for use in knee replacement surgery comprising a tibial base plate (14) which, in use, engages a tibia (200), and a tensioning element (33), (34) operable, in use, to engage between the tibial base plate (14) and a femur (300) to set the gap between the tibial base plate (14) and the femur (300) when the femur (300) and tibia (200) are in extension.

19 Claims, 14 Drawing Sheets

(51) Int. Cl.
*A61B 90/00* (2016.01)
*A61B 17/17* (2006.01)

(56) References Cited

U.S. PATENT DOCUMENTS

| | | | | |
|---|---|---|---|---|
| 5,597,379 | A | * | 1/1997 | Haines ................ A61B 17/1764 606/80 |
| 5,688,280 | A | | 11/1997 | Booth, Jr. et al. |
| 5,800,438 | A | * | 9/1998 | Tuke .................... A61B 5/1076 606/102 |
| 5,911,723 | A | * | 6/1999 | Ashby .................. A61B 17/154 606/88 |
| 6,013,081 | A | * | 1/2000 | Burkinshaw ......... A61B 17/155 606/102 |
| 6,077,270 | A | * | 6/2000 | Katz .................... A61B 17/154 606/102 |
| 2002/0029045 | A1 | | 3/2002 | Bonutti |
| 2005/0020941 | A1 | * | 1/2005 | Tarabichi ............. A61B 5/1071 600/587 |
| 2005/0256527 | A1 | * | 11/2005 | Delfosse .............. A61B 17/025 606/88 |
| 2007/0293868 | A1 | * | 12/2007 | Delfosse .............. A61B 17/025 606/88 |
| 2008/0154270 | A1 | | 6/2008 | Haines et al. |
| 2008/0188934 | A1 | * | 8/2008 | Moser .................. A61B 17/025 623/13.13 |
| 2009/0043310 | A1 | * | 2/2009 | Rasmussen .......... A61B 17/025 606/88 |
| 2009/0270869 | A1 | * | 10/2009 | Colquhoun .......... A61B 17/025 606/88 |
| 2010/0198275 | A1 | * | 8/2010 | Chana .................. A61B 17/155 606/86 R |
| 2010/0241126 | A1 | * | 9/2010 | Ghijselings .......... A61B 17/025 606/88 |
| 2012/0172881 | A1 | * | 7/2012 | Hutchison ............ A61B 17/025 606/88 |
| 2012/0259342 | A1 | * | 10/2012 | Chana .................. A61B 17/155 606/88 |
| 2014/0288563 | A1 | * | 9/2014 | Claypool ............. A61B 17/025 606/88 |
| 2016/0106409 | A1 | * | 4/2016 | Moholkar ............ A61B 17/025 606/90 |
| 2016/0278754 | A1 | * | 9/2016 | Todorov ............... A61B 17/025 |
| 2017/0007225 | A1 | * | 1/2017 | Ferro ................... A61B 17/025 |

FOREIGN PATENT DOCUMENTS

| | | |
|---|---|---|
| EP | 1442712 A1 | 8/2004 |
| EP | 1634536 A2 | 3/2006 |
| EP | 2138107 A1 | 12/2009 |
| EP | 2237014 A2 | 10/2010 |
| EP | 2581049 A1 | 4/2013 |
| WO | 2010111678 A2 | 9/2010 |
| WO | 2012020460 A1 | 2/2012 |

* cited by examiner

ASSEMBLIES FOR USE IN KNEE REPLACEMENT SURGERY

The present invention relates to improvements in or relating to assemblies for use in knee replacement surgery. Examples of the invention address a need for balancing soft tissues in conjunction with appropriate bone resection.

DEFINITION OF TERMS

For the sake of the present application, vertical and/or varus and valgus rotational movement of a femoral cutting block or femoral rotation block may mean vertical and/or rotational movement of the cutting block itself, or movement of the block with reference to a femur.

BACKGROUND

Prosthetic knee replacement involves placing a metallic prosthesis at the end of the femur and tibia. The surgical preparation requires making one cut on the tibia, and a number of cuts on the femur using traditionally available tools.

However, a significant proportion of patients who undergo knee replacement surgery have unsatisfactory results. This leads to patients returning with pain, complaints etc, which in turn clogs up waiting lists, leads to pressure on knee surgeons who are overwhelmed with patients, and frequently leads to patients undergoing repeat replacement surgeries. Because knee surgeons are often under severe time pressure, quality control is lost, leading to still more unsatisfactory results from surgery.

One of the main reasons for this is failure to adequately balance soft tissues, (in particular lateral and medial ligaments) of the knee during surgery—if ligaments are not appropriately balanced, even if the bony cuts are made correctly (such that they appear pleasing on X-ray), the patient may experience extremely significant pain if a ligament(s) is overly tensioned as a result of the procedure, or may experience lessening function of the knee if a ligament(s) is loosened excessively.

Frequently ligament(s) are released during knee replacement procedures. This is done by making small releases to the ligament to loosen it from the bone. Unfortunately ligaments are often released too much, or too little, and many operations are conducted with little control over ligament balancing. Often this is left simply to the desire of the surgeon, with little or no templatized control. As stated, even if bony cuts appear pleasing on an x-ray, overly tensioned ligaments, or overly loosened ligaments, may lead to unsatisfactory results for a patient and may require repeat surgery. Repeat surgery has lower likelihood of success, thus further aggravating waiting lists and pressure on surgeons.

Presently available devices allow ligament balancing based on changes to femoral rotation. No tool, instrument, device, or assembly is available that can balance lateral and medial gaps appropriately during a procedure and appropriately align the prosthesis in extension and flexion by altering the bony cuts and/or ligaments, within acceptable limits, in an integrated fashion. No such instrumentation could simultaneously guarantee correct gap measurement between tibial and femoral resection so that the prosthesis can be correctly and appropriately fitted.

Until an industry standard is achieved via correct instrumentation and measuring, unacceptable results for knee replacement surgery will continue, and little quality control, especially globally across the knee replacement industry, will be achieved, which will lead to further problems for patients, knee surgeons, and health systems.

SUMMARY

The present invention is defined by the accompanying claims, to which reference should now be made.

Examples of the present invention seek to provide a solution to the above problem(s) by providing, (for resection of the femur in extension) a knee ligament tensioning device comprising: a tibial base plate; a tensioning system for tensioning lateral and medial ligaments, the tensioning system comprising means for tensioning the lateral and medial ligaments. There may be a measuring system to measure the lateral and medial ligament gaps when the ligaments are tensioned by the tensioning system, to facilitate appropriate ligament balancing prior to resection of a femur, the measuring system comprising means for engaging lateral condyle and medial condyle of the femur.

The examples are used following proximal tibial resection.

The tensioning means (which may be a central limb) applies pressure to the femur, tensioning the ligaments. If a ligament is particularly tight, it may be released by the surgeon within appropriate limits, thus balancing the ligaments. The femur is resected at a degree of rotation, and at a height, appropriate for the ligaments. This is essential for long-term good results for patient. This substantially templatizes this process.

Examples also provide:

An assembly for use in knee replacement surgery, comprising:
  a tibial base plate;
  a femoral block; and
  an attachment solution for attaching the cutting block to the tibial base plate.

The tibial base plate may come as part of a wider device, which may, for example, further comprise a main body, handle, etc, and may comprise: means for tensioning lateral and medial ligaments; means for engaging lateral and medial condyles; or both. In such a case, thus the assembly may feasibly be provided as a device (the device comprising the tibial base plate); a femoral block; and an attachment solution for attaching the cutting block to the tibial base plate.

The attachment solution may comprise a connecting element to attach the femoral block to the tibial base plate, or may be a direct attachment solution, whereby the femoral block attaches direct to the tibial base plate, without need for a connecting element.

Similarly, it is thought a block that is both substantially vertically upwardly and downwardly, and rotationally varusly and valgusly movable with respect to a femur, is novel. Examples also provide: a distal femoral cutting block, comprising: a block body; a cutting slot; an attachment means for attaching the distal femoral cutting block to a femur that facilitates varus and valgus rotation; and a vertical adjustment mechanism to facilitate vertical movement of the cutting slot relative to the attachment means, the distal femoral cutting block thus configured to facilitate both; varus and valgus rotation of the cutting slot with reference to the femur; and vertical adjustment of the cutting slot with reference to the femur.

Both the vertical movement of the attachment means, and rotational movement of the attachment means may be divorced from a main block body of the cutting block, which main block body preferably comprises the cutting slot. It is feasible in alternate embodiments that just one of: vertical movement of the attachment means; rotational movement of the attachment means, is divorced from the main block body.

This may be achieved by a rotatable element which has apertures for receiving pins pinned into the femur, which rotatable element may be vertically slidable via an intermediate movement facilitation element.

Examples of the present invention will now be more particularly described, with reference to the accompanying drawings, and by way of example only, and in no way limiting the scope of the invention, in which.

Before commencing a detailed description of the drawings (and hence of the invention), it is important to realise at what point during a knee replacement procedure the apparatus in used.

It will be well known to those with skill in the art that a knee replacement procedure typically begins with opening of the knee to gain access to internal structures, which may require a slight release of the ligament(s). Once the knee is opened, the tibia is fastened for cutting, the knee is put in flexion, and bone resection typically begins with proximal tibial cut, where the tibia bone is resected in a substantially horizontal axis. In order to achieve this, the tibia is fastened and a tibial cutter is used to resect the tibia, typically with an oscillating saw.

This first course of action is endorsed by the present invention, although it must be stated that release of ligament(s) in order to gain access to the knee should be kept to a minimum to retain ligament tension where possible. Unfortunately, even at this early juncture, ligament(s) are excessively released by some surgeons, (which is achieved by gently releasing the ligament(s) from the bone). This may affect ability to adequately balance soft tissues with bony cuts.

At this point, distal femoral cut is often made, which destroys vast opportunities for ligament balancing. Rather than immediately resecting the femur in this way (which may look like an accurate cut on later X-rays, but in fact lead to discomfort for a patient due to lack of adequate and appropriate soft tissue balancing), the present invention endorses balancing soft tissues with the knee in extension before any femoral cut is made. This is extremely important—an added benefit being that the invention can be similarly used/modified for use similarly in balancing medial and lateral ligaments prior to making femoral cuts in flexion.

Figure 1:
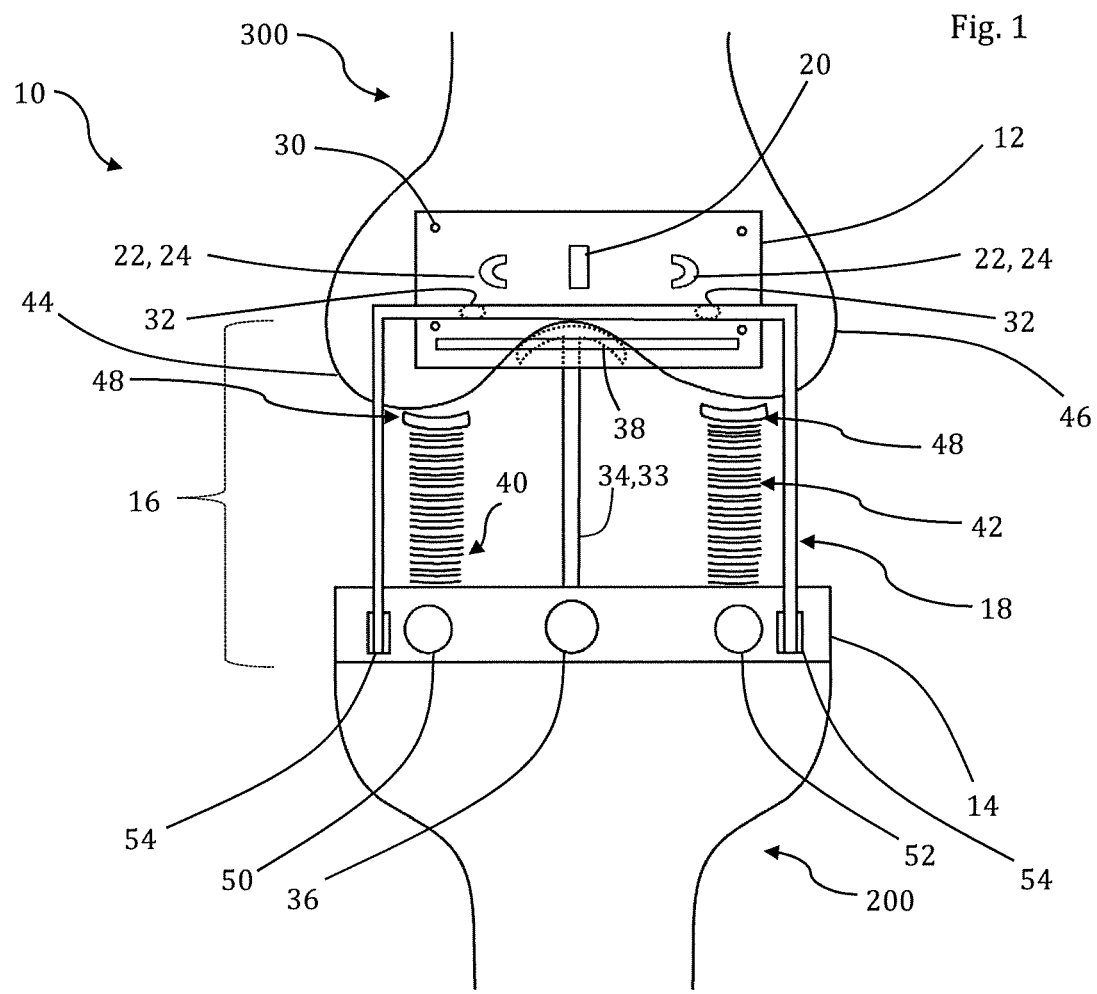
FIG. 1 is a frontal view of a right knee where an instrument assembly for use in knee joint replacement surgery is being used in extension for balancing of ligaments and positioning of a distal femoral cutting block in preparation for appropriate resection of a femur with reference to ligament balancing.

Thus, referring to the drawings, there is shown, in FIG. 1, (and also FIG. 4), an instrument assembly 10 for use in knee joint replacement surgery, comprising a distal femoral cutting block 12, a tibial base plate 14, a tensioning system 16 for tensioning lateral and medial ligaments, a measuring system, and a connecting element 18 for fixedly connecting the tibial base plate 14 and distal femoral cutting block 12, for use in resection of femur with knee in extension.

The knee (a right knee in frontal view) is in extension, and the tensioning system 16 has been fitted into the gap between the resected tibia 200 and the femur bone 300, which has yet to be resected. The tibial base plate 14 is placed against the resected tibia 200 and may be held in place by the roughness of the neighbouring surfaces, or by a fixing. The tibial base plate 14 may be generic in shape or tailored to the specific patient. The distal femoral cutting block 12 is to be positioned appropriately to optimise height and angulation of the femoral cut with reference to soft tissue (ligament) balancing. In order to achieve this, the distal femoral cutting block 12 is fixed loosely to the femur—it is not securely and fixedly fixed. It has an ability to move not only upward and downward on a substantially vertical axis, but also, crucially, to move varusly and valgusly with reference to the femur 300. Such varus and valgus movability of the cutting block 12 is thought to be novel.

Figure 2:
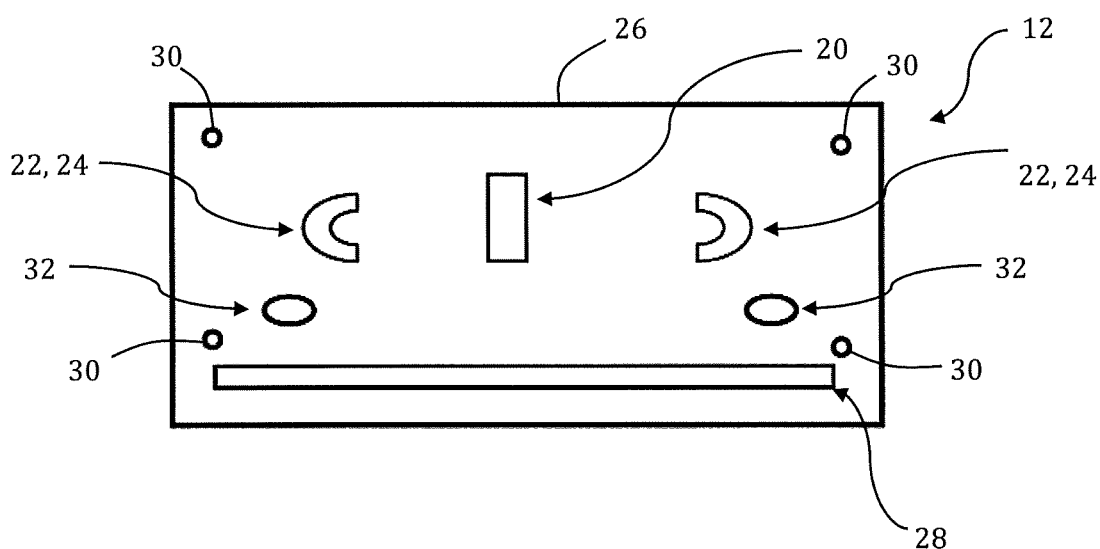
FIG. 2 is a frontal view of a distal femoral cutting block which may be used in accordance with the assembly of FIG. 1.

In one example, the distal femoral cutting block 12 may simply have a large aperture (large with respect to any pin and the like that is holding it to the femur 300), so that it is loosely fixed to the femur 300, and therefore movable whilst fixed. An example of aperture configuration for the cutting block to achieve this vertical and rotational movability is shown in FIG. 2, where the aperture configuration comprises at least three apertures, there being provided: a vertical movement aperture 20, configured to facilitate loose fixing of the cutting block 12 to the femur 300, and to facilitate substantially vertical upward and downward movement of the block whilst the cutting block 12 is loosely fixed to the femur 300; a varus rotation aperture 22, configured to facilitate loose fixing of the cutting block 12 to the femur 300, and to facilitate rotation of the cutting block 12 whilst the block 12 is loosely fixed to the femur 300; and a valgus rotation aperture 24, configured to facilitate loose fixing of the cutting block 12 to the femur 300, and to facilitate rotation of the block 12 whilst the block 12 is loosely fixed to the femur 300, the apertures thus facilitating movement and rotation of the distal femoral cutting block 12 with respect to the femur 300. The distal femoral cutting block 12 also comprises a block 26, a cutting slot 28 for directing cutting with an oscillating saw, and at least two secure fixation apertures 30 (and more preferably four) for fixing the cutting block 12 fixedly to the femur 300 once correct ligament balancing has been achieved. There are also shown two connection ports 32, which, as will be shown, is a feasible method for facilitating connection of the connecting element 18 to the cutting block 12 if the connecting element 18 includes connection protrusion(s), although any other method, such as a magnetic strip, may be used to connect the connecting element 18 and the cutting block 12, without limiting the scope of the present invention.

In the shown embodiment of the distal femoral cutting block 12, as shown in FIG. 2, the cutting block 12 can be used for resection of the femur 300 on either knee, the varus and valgus rotation apertures 22, 24 being interchangeable.

Figure 4:
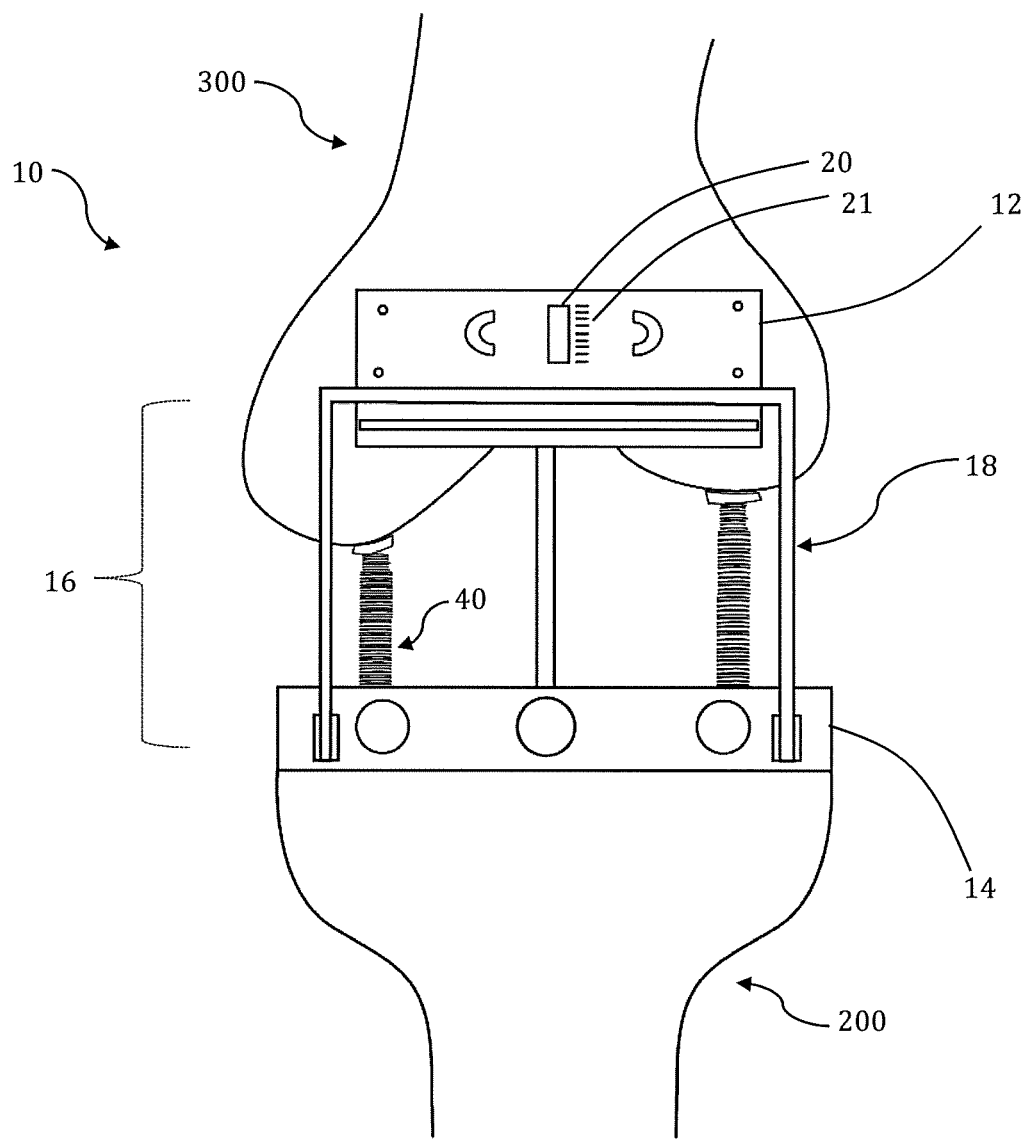
FIG. 4 is a frontal view of the assembly of FIG. 1 in use where there is shown severe lateral ligament tension.

There may be provided marking(s) for any of the apertures to denote height and/or rotation measurement(s) of the cutting block 12. Thus there is shown in FIG. 4 measurement markings 21 for the vertical movement aperture, which markings, (and thus dimensioning of the aperture 20), may be provided within acceptable industry limits and/or standards. Thus measurements of vertical placement and varus and valgus rotational angle of the cutting block 12 may be indicated to a user, and placement and angle of femoral cut may be limited to within an industry standard by dimensioning of the vertical and/or rotational aperture(s). Similarly marking(s) and/or measurements may be provided for any of the apertures.

Referring to FIG. 2, it can be seen that the secure fixation apertures 30 are significantly slighter in girth than the vertical movement 20 and rotation 22, 24 apertures. The apertures are of such girth that, once the cutting block 12 is fixed to the femur 300, (preferably via pin(s)), the girth and dimensioning of the apertures is significantly larger than girth of the, preferably, pin(s). Therefore the cutting block 12 is vertically and rotationally movable with respect to the femur 300. Thus the cutting slot 26 of the cutting block 12 is also upwardly and downwardly movable, as well as varusly and valgusly rotatable with respect to the femur 300.

As will be shown, in one example of the assembly, tensioning of the ligaments is used to appropriately move and position the distal femoral cutting block 12, and thus the cutting slot 28, and a connecting element 28 is used to connect the tibial base plate 14 to the distal femoral cutting block 12 so that correct gap measurement in extension between resected tibia 200, and resected femur, can be achieved.

In a most basic embodiment, it is feasible that the distal femoral cutting block 12 has simply one large aperture for loose and movably fixing to the femur 300. However, such a basic aperture configuration may lead to excessive movement of the cutting block 12 whilst fixed to the femur 300, which may be problematic for a surgeon, and/or simply unprofessional in use. Furthermore, such a basic configuration where the cutting block 12 is excessively loose and movable provides a further problem; there are acceptable limits, well known to those with skill in the art, both for height positioning of the cutting slot 26 for performing femoral resection, and for degree of varus and valgus rotation and/or angulation of the femoral resection cut.

A solution to this, as shown in the example of the distal femoral cutting block as shown in FIG. 2, is an aperture configuration which both facilitates vertical and rotational movement of the cutting block 12, and simultaneously limits vertical and/or rotational movement of the cutting block 12, thus guaranteeing resection of the femur 300 in extension in carried out within acceptable limits. Thus it can be seen, the varus and valgus rotation apertures 22, 24, which are shown in crescent-shape although they or each may feasibly be dimensioned differently, facilitate rotational movement of the cutting block 12, but also limit rotational movement of the cutting block 12. Preferably the rotation aperture(s) 22, 24 are configured to limit rotation of the block within acceptable limits that are well known within the industry, for example 3 to 7 degrees, thus reassuring users (surgeons), the aperture(s) being configured so that unpredictable results (and inappropriate femoral resection) with the cutting block are avoided.

Similarly, the vertical movement aperture 20 both facilitates substantially vertical upward and downward movement of the cutting block 12 with respect to the femur 300, and also limits upward and downward movement, preferably within well-known industry standards, such as no more than 4 mm upward and 4 mm downward movement, and more preferably limited to 3 mm upward and 3 mm downward movement with respect to the femur 300. Preferably there are provided markings and/or indicators on the cutting block 12 (and more preferably about the rotation aperture(s) 22, 24), so that angle of rotation of the cutting slot 26 (and thus the soon-to-be-carried-out femoral cut) is indicated to a user (surgeon). Similarly, preferably there are provided markings and/or indicators on the cutting block (and more preferably about the vertical movement aperture 20), so that vertical positioning of the cutting slot 12 (and thus the femoral cut) with respect to the femur 300 is indicated to a user (surgeon). Thus there is preferably provided control for the user, with results guaranteed to fall within acceptable limits. There is shown in FIG. 4 an example of vertical movement markings 21, which may be provided by way of millimeter readings. Such markings and/or indicators may be provided electronically, mechanically, via computer, navigation, or any other method, etc.

It is thought that capacity for varus and valgus rotational movement of a loosely fixed distal femoral cutting block 12 is novel. It is desirable that the distal femoral cutting block 12 is both vertically upward and downwardly movable, and varusly and valgusly rotationally movable with respect to the femur. Thus the present example 10 provides a solution to lack of both vertical and varus and valgus rotational movement capacity for the cutting block 12, with reference to the femur 300.

It is feasible there is provided only one rotation aperture 22, 24 for the cutting block 12, in which case it is possible a separate cutting block 12 may be required for resection of left and right patient femur. It is feasible the cutting block 12 is reversible, with there being provided two cutting slots 26; there being provided one cutting slot 26 at a top of the cutting block 12, and one cutting slot 26 at a bottom of the cutting block 12, so that the cutting block is reversible for use for resection of right, and left, femur, which may be useful, particularly if only one rotation aperture 22, 24 is provided. The cutting block 12 could feasibly be configured so that it can be turned over (flipped) for use on either left or right knee for resection of the femur 300.

Referring back to FIG. 1, the assembly is shown where the distal femoral cutting block 12 has been loosely fixed to the femur 300. It will be obvious to those with skill in the art that the distal femoral cutting block 12 is typically fixed to the femur 300 via use of an intramedullary rod, and a distal femoral cutting block assembly guide. Such instruments are well known to those with skill in the art.

Figure 3:
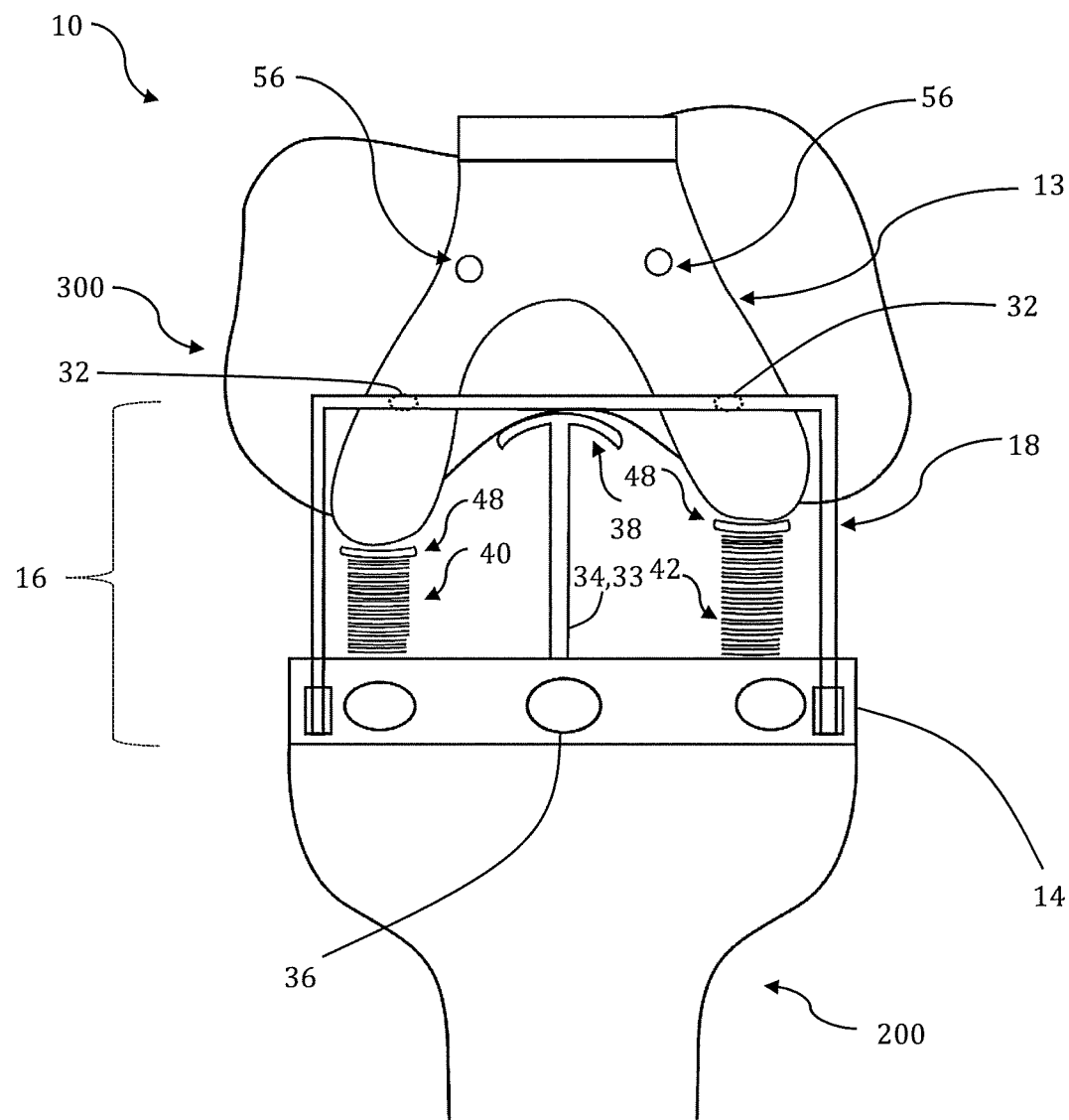
FIG. 3 is a frontal view of an assembly used in flexion on a right knee, and where a distal femoral cutting block has been substituted by a femoral rotation block.

A tibial base plate 14 is placed and/or attached to a resected tibia 200. The base plate 14 may be of any height, and substantially of any dimension for the purpose. In FIG. 1, FIG. 3, and FIG. 4, the base plate 14 provides a platform for the tensioning system 16, which comprises a central limb 34 that is either attached, or attachable, to the tibial base plate 14, extending therefrom. Preferably there is provided a means for adjusting extension 36 of the central limb 34 so that extension of the central limb 34 is adjustable, the tensioning system 16 thus configured for the central limb 34 to engage, and apply pressure to, an intercondylar notch of the femur 300, thus tensioning lateral and medial ligaments. (The ligaments are not depicted in the drawings).

The means for central limb adjustment 36, which is shown in FIGS. 1, 2, 4 as a mechanical dial 36 that can be turned by a user to extend (and retract) the central limb 34, may be provided about the base plate 14. It is also feasible that the means for adjusting the central limb is a self-adjusting means, such as a spring-loaded mechanism, whereby the central limb 34 is naturally tensioned, and thus extends and engages the intercondylar notch when released. The central limb adjusting means may be mechanical, digital, analogue, electronic, computerized, etc, or any other means for adjustment. If the central limb 34 is spring-loaded, it may be adjustable by retraction towards the tibial base plate 14. It is feasible there is a retraction mechanism for the central limb 34 so that the central limb 34 can be retracted toward the base plate 14, and so that, once released, it spring-loadedly releases and extends, thus engaging, and applying pressure to, the intercondylar notch of the femur 300. It is feasible the central limb is pre-configured to engage intercondyllar notch at a pre-determined, and/or limited, pressure.

There may be provided a shaped tip 38 for the central limb 24, which may be convex, so that it securely engages and applies pressure to, the intercondylar notch. It may have multiple convex prongs for so doing. Thus it can be seen that centralised pressure is applied to the femur 300 from the at least one of: attached; attachable central limb 34. This tensions lateral, or medial ligaments, or both.

Figure 5:
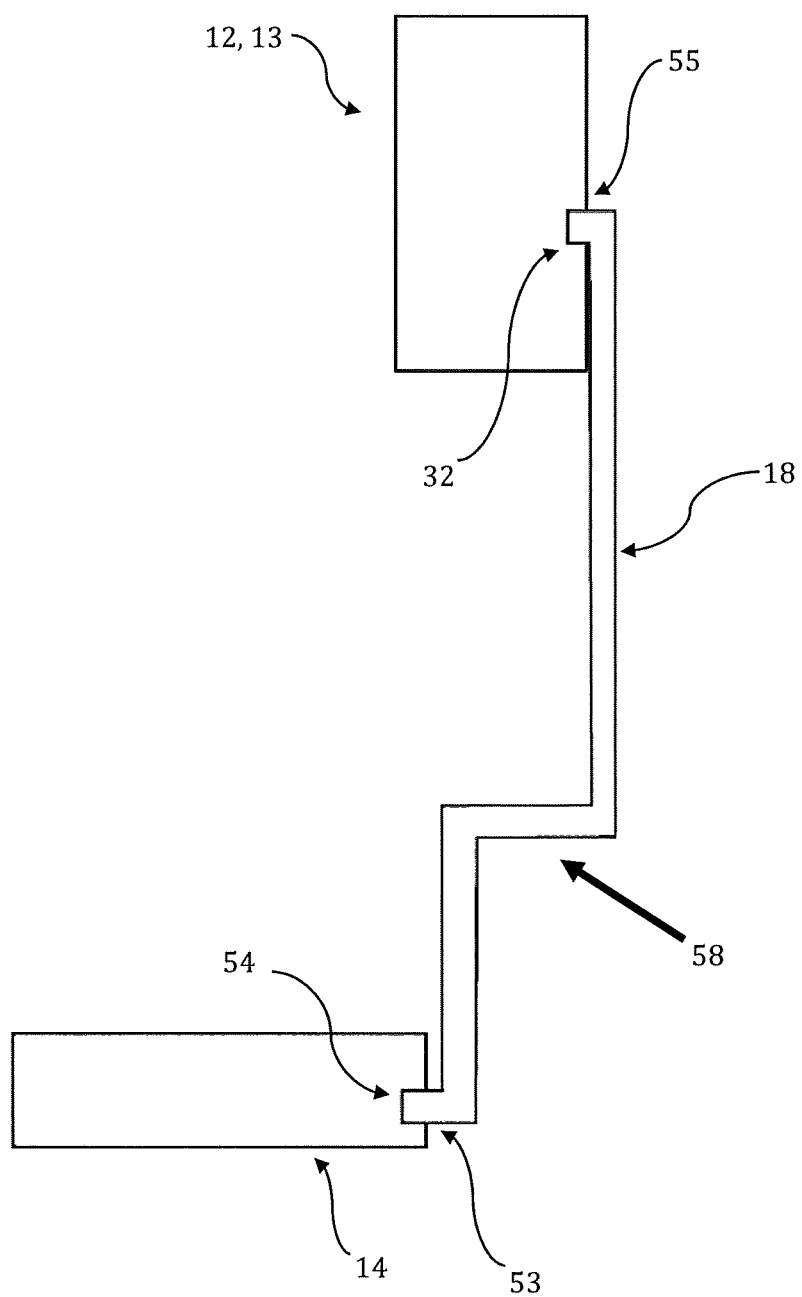
FIG. 5 is a side-on view of a connecting element for connecting a tibial base plate and a distal femoral cutting block or femoral rotation block, wherein the connecting element is anteriorly angulated or curved.

WO2012156806 A1 (Medacta) discloses in FIG. 5, an element G2 that prises open a gap between tibia and femur, thus tensioning lateral and medial ligaments. However, there is no adjustment for the tensioner; this is potentially damaging to ligaments. If the gap opened by device G2 overtensions a ligament, the ligament may be damaged. The ligament tensioning system 16 of the present example incorporates a central limb 34 of adjustable length, which may be preconfigured and/or limited to engage the intercondylar notch (and thus the femur 300) at a pre-configured pressure that is acceptable and within appropriate limitations so that ligaments are not damaged.

In FIG. 1, FIG. 3, and FIG. 4, the tibial base plate 14 also provides a platform for a measuring system, said measuring system comprising a lateral gap measuring element 40; and a medial gap measuring element 42, the gap measuring elements 40, 42 at least one of: attached; attachable, to the tibial base plate 14 and extending therefrom, the lateral gap measuring element 40 configured to engage lateral condyle 44 of a patient, the medial gap measuring element 42 configured to engage medial condyle 46 of a patient, the measuring elements 40, 42 thus substantially indicating lateral and medial gaps, and substantially denoting lateral and medial ligament tension.

The measuring elements 40, 42 may be substantially spring loaded so that, when engaged with lateral and medial condyles, lateral and medial ligament tension is spring-loadedly indicated to a user. However, it is feasible, in a most basic example, that the gap measuring elements 40, 42 are simply extendable members, feasibly manually extendable, so that they can be extended to engage lateral and medial condyles.

The measuring elements may have shaped heads 48, which may be resiliently movably oriented, so that the shaped head movably adjusts to more securely engage a condyle. Thus the measuring elements 40, 42 may be of substantially flexible composition.

The measuring system may further comprise a measurement reading means, so that lateral and medial gaps are readable by a user. Said measuring reading means may be incorporated by way of a lateral gap reader 50 and a medial gap reader 52, which gap readers 50, 52, may be mechanical. However, measurement reading may be provided by any means, such as electronic, computerised, etc. The intent is to communicate lateral and medial gap measurements to a user. This may be achieved in many, or any, way(s), which will be obvious to those with skill in the art, in no way limiting a scope of the present invention.

There may be provided a retraction mechanism for the gap measuring elements 40, 42, so that, if spring-loadable, the gap measuring elements can be fixedly retracted toward the tibial base plate 14. Such a mechanism, which fixedly retracts the gap measuring elements close to the tibial base plate, may aid placement of the gap measurer and tensioner into the gap between femur 300 and resected tibia 22. It will be obvious to those with skill in the art that gaining access to the gap is often challenging; thus retractable gap measuring elements may aid placement, at which point, the measuring elements can be released (if spring-loadedly retracted), or extended (if not spring-loadedly retracted) for engaging with lateral and medial condyles 44, 46.

If extreme tension is witnessed in one or both ligaments (which will be shown via shortened length of a gap measuring element 40, 42), ligament release may be undertaken by a user (surgeon) as a first means of balancing ligaments.

Next, in the shown example, a connecting element 18 is provided for fixedly connecting the tibial base plate 14 to the distal femoral cutting block 12 whilst the cutting block 12 is loosely fixed to the femur 300, so that, via the aperture configuration of the distal femoral cutting block 12, the cutting block 12 is substantially vertically movable, and varusly and valgusly rotatably positionable with respect to correct ligament balancing, and securely fixable to the femur 300 for resection of the femur 300 via the cutting slot 26.

It is feasible the connecting element 18 is attached and/or used after first ligament balancing and release has been undertaken by a user.

The connecting element 18 acts as a framework, effectively providing a template for positioning of the distal femoral cutting block 12, the cutting block 12 now vertically and rotatably movable due to ligament tension.

The connecting element 18 also creates a, preferably pre-determined, gap between tibia 200 and femur 300, so that, post resection, the gap is correct for introduction of a knee prosthesis. Preferably, desired gap for the prosthesis is 20 mm. it is feasible gap may be desired to be greater (or feasibly smaller) than 20 mm, dependent on prosthesis. Thus the connecting element 18 is dimensioned appropriately so that correct gap between resected and resected tibia is guaranteed, so that knee replacement prosthesis is placeable in the gap.

It is desirable (and may be essential) at this point that visibility of inner structures of the knee is not obscured by the connecting element 18. Thus the connecting element 18, as shown, is a frame, thus not obscuring visibility. However, it is feasible the connecting element 18 is of substantially any shape and/or dimension for the purpose. The connecting element 18 could be a connecting plate, in which case, if it is dimensioned in such a way that it would obscure visibility of structures of the knee, it is desirable if it is of transparent materials, thus not substantially obscuring visibility for a user. Thus it may be, for example, of transparent plastics materials. It is a substantially centrally hollowed frame in FIGS. 1, 3, 4.

If the connecting element 18 is not previously attached to, or an integral part of, the tibial plate 14, a plate attachment solution 54 is required. This may be carried out in any way to attach the connecting element 18 to the base plate 14. There may, for example, be a clip on the base plate 14 to securely hold the connecting element 18.

Similarly, in the shown example, a block attachment solution is required for securely attaching the connecting element 18 to the distal cutting block 14 for resection of the femur in extension (and, as will be shown, for attaching the connecting element 18 to a femoral rotation block for resection of the femur in flexion). This may be carried out in any way, in no way limiting the scope of the present invention. In FIG. 1 and FIG. 2, the distal femoral cutting block 12 is shown with receiving ports 32, which are configured to receive protrusions on the connecting element 18. Thus when the protrusions are received by the receiving ports (which may simply be holes of pre-determined dimension to receive the protrusions) the connecting element 18 is securely connected to the distal femoral cutting block. Any means of connection may be utilised. It is feasible there is provided a magnetic strip on the cutting block 12 (or femoral rotation block 13), so that the connecting element 18 is magnetically attached to the cutting block 12, and vice versa.

Thus it can be seen that the tibial base plate 14 and the distal femoral cutting block 12 are securely connectable via the connecting element 18.

Connecting of distal femoral cutting block 12 to tibial base plate 14 results in positioning of the distal femoral cutting block 12 (and thus the cutting slot 26), defined by ligament tension. It is thought that such movability of the cutting block 12, in both a substantially upwardly and downward, and a varus and valgus orientation, is novel.

Thus orientation of femoral resection cut via the cutting slot 26, with balance to ligaments, is achieved. This is extremely desirable for appropriate resection of the femur 300 with respect to ligament balancing.

There is shown in FIG. 3 the assembly where the assembly is used for resection of the femur 300 in flexion. It will be well known to those with skill in the art that a cutting block in not initially attached to the femur for resection in flexion. Instead a femoral rotation block 13 is utilised, and loosely held. Thus the distal femoral cutting block 12 is substituted for a femoral rotation block 13. The femoral rotation block 13 has at least two guide apertures 56, so that once desired positioning of the rotation block 13 is achieved, guide holes can be drilled into the femur 300 through the guide apertures 56 to facilitate correct positioning of a soon-to-be-attached cutting block via the guide holes.

The assembly functions exactly the same as shown in FIG. 1 when used in extension, using the tibial base plate 14, tensioning system 16, measuring system, and connecting element 18, which again securely connects the base plate 14, now to the femoral rotation block 13, rather than the distal femoral cutting block 12.

Similar ligament balancing is undertaken. Once desired positioning and balancing is achieved, guide holes are drilled through the at least two guide apertures 56. The guide holes are used for fixation of a, preferably 4-in-1, cutting block, which facilitates resection of the femur in flexion, which requires a plurality of bony cuts.

There is shown in FIG. 5 a connecting element 18 with anterior angulation. The tibial base plate 14 and a femoral block 12, 13 (which may be either a distal femoral cutting block 12 (for resection of the femur in extension), or a femoral rotation block 13 (for resection of the femur in flexion)) are connected by the connecting element 18. The connecting element 18 is attached to the tibial base plate 14 via an attachment solution, which is preferably provided by way of a protrusion 53 from the connecting element 18 that is received by a receiving port 54 in the base plate 14, (although any attachment method may be used). The connecting element 18 has a protrusion 55 that is received by a receiving port 32 in the femoral block 12, 13. (Other attachment method(s) may be used).

As shown, anterior angulation 58 of the connecting element 18 may be required due to dimensioning of the femoral block 12, 13. The anterior angulation 58 may be curved, etc. The intent is that the connecting element 18 is shaped in such a way that the tibial base plate 14 and the distal femoral cutting block 12 or femoral rotation block 13 are fixedly connected.

It is feasible the connecting element 18 connects to the femoral block 12, 13 via a base of the block 12, 13. Nevertheless, anterior angulation may be required.

In Use

The example will now be described in use, with reference to FIG. 4, for use in resection of the femur in extension, in no way limiting the scope of the invention.

The example is shown wherein there is extreme tightness of lateral ligament. This is shown by the short extension of lateral gap measuring element 40. If the lateral ligaments are found to be tight, an attempt is made to release the ligament first within acceptable limits. Only when the ligaments on the lateral side has been released adequately will bony cuts be made. With the present example the user will be able to gauge the amount of varus/valgus angulation and the bony cut he/she is about to make before making the cut thereby helping the results of the knee replacement. As shown in FIG. 4, the cutting slot 26 is angled (rotated) with respect to the femur 300 so that more bone is cut on a lateral side of the femur, thus balancing ligament tension. Resecting more bone on a side with tight ligaments in known to provide better long term results for patients who undergo knee replacement.

The examples described above are provided by way of example only, and various other modifications will be apparent to persons skilled in the art without departing from the scope of the invention as defined by the appended claims.

Description of a Second Example

A second example will now be more described, as shown in FIGS. 6 to 20.

Referring to FIGS. 6 to 20 (excluding FIGS. 10, 19, 20, which shows the femoral blocks 12, 13 alone), there is shown a knee ligament tensioning device, comprising: a tibial base plate 14; a tensioning system for tensioning lateral and medial ligaments. There is also a measuring system to measure the lateral and medial ligaments when the ligaments are tensioning by the tensioning system, the measuring system comprising means for engaging lateral condyle and medial condyle of a femur.

Word 'system' for tensioning system and measuring system is used broadly and should not be seen as necessarily indicating complexity or limitation on the invention. A tensioning system, for example, may be as simple as comprising a means for tensioning lateral and medial ligaments, or may, in more preferred embodiments, be significantly more complex, comprising further element(s).

In the shown example, the knee ligament tensioning device further comprises a main body 60. The main body 60, (shown by way of example only), has a front first side 62, and a front second side 64, with a front central gap 66 in between the front first side 62 and front second side 64. It also has a back first side 68 and a back second side 70, with a back central gap 72 in between the back first side 68 and back second side 70. Such a configuration for the (or any) main body 60 is shown by way of example only.

There is shown a handle 75 for handling the device, which is preferably attached or part of the main body 60.

In the shown example, the tibial base plate 14 is shown attached to the main body 60 via a sleeve 74. The sleeve 74 and tibial base plate together form a head of the knee ligament tensioning device. The attachment may be permanent (ie the head may be attached at manufacture so that the head (including the tibial base plate 14) are not removable by the user (surgeon, etc)), or, in alternate embodiments, it is feasible the tibial base plate 14 is removably attachable to the main body 60 (either directly removably attachable, or removably attachable by way of the head (ie the tibial base plate 14 and sleeve 74 being removably attachable from the main body 60). Thus it is feasible that a separate knee ligament tensioning and measuring device may be required for use on left and right knee (in embodiments where the tibial base plate 14 is non-removable), or that alternating tibial base plates 14 may be removably attachable to the main body 60 (either directly or with the sleeve 74 as part of a head) for use with alternating knees. Thus there could be provided a universal main body, with left and right sided removable base plates 14. (Tensioning element(s) and gap measuring element(s) may also be removably attachable). Thus it is feasible any or all of: tensioning element(s), means for engaging lateral and medial condyles (which may include lateral and medial gap measuring element(s)) and tibial base plate may be removably attachable and thus there may be provided a left and right-sided version of any or all of these parts that can be interchangeably attached to a universal main body 60.

Therefore it is also feasible that the universal main body could be attachable to a side specific baseplate, measuring element(s) and tensioning element(s) at the manufacturing stage. Thus it is feasible to provide the user the facility to use the knee ligament tensioning and gap measuring device in a modular fashion so that the universal body can be assembled to the tensioning element(s), measuring element(s) and gap measuring element(s).

Figure 9:
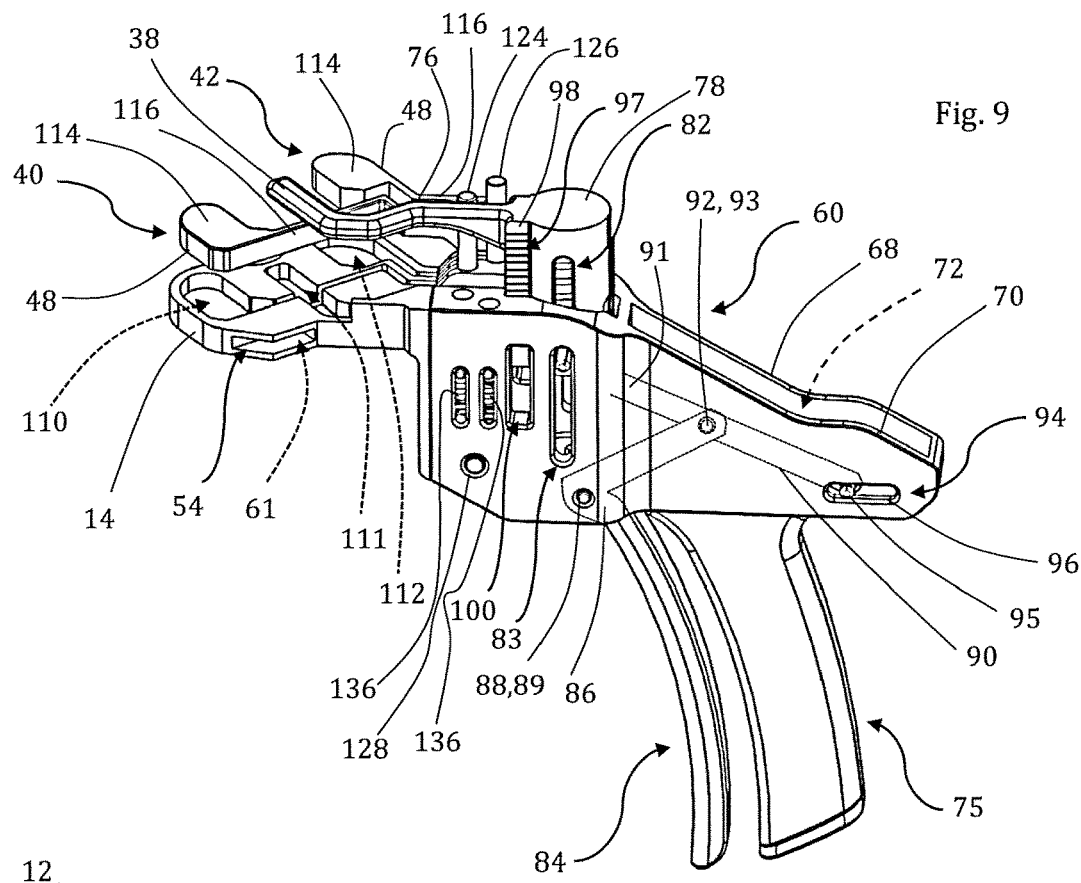
FIG. 9 is a lateral side perspective view of the example of FIG. 6 wherein the central tensioning element as well as lateral and medial gap measuring elements are also raised.

In the shown example, the tibial base plate 14 has a lateral recess 110 for a lateral gap measuring element 40 when the lateral gap measuring element 40 is in a (preferably locked) low position, and a medial recess 112 for a medial gap measuring element 42 when the medial gap measuring element 42 is in a (preferably locked) low position. The recesses 110, 112 are best shown in FIG. 9, where the gap measuring elements 40, 42 are shown raised from the base plate 14. The recesses, in the shown example, are particularly prevalent where they are dimensioned for housing shaped heads 48 of the gap measuring elements 40, 42.

There is also shown a central recess 111 for housing a central tensioning element 33 when in a low position. (Again, the central recess is best shown in FIG. 9, where the central tensioning element 33 is shown raised from the tibial base plate 14, or FIG. 8, where central tensioning element 33 only is raised, with gap measuring elements 40, 42 recessed.

In the shown example, the base plate 14 has a plate attachment solution 54 for attaching a connecting element 18 to the tibial base plate 14, which solution, in the shown example, is a receiving port. The receiving port comprises a cavity 61 into which the connecting element 18 can be connected.

Figure 10:
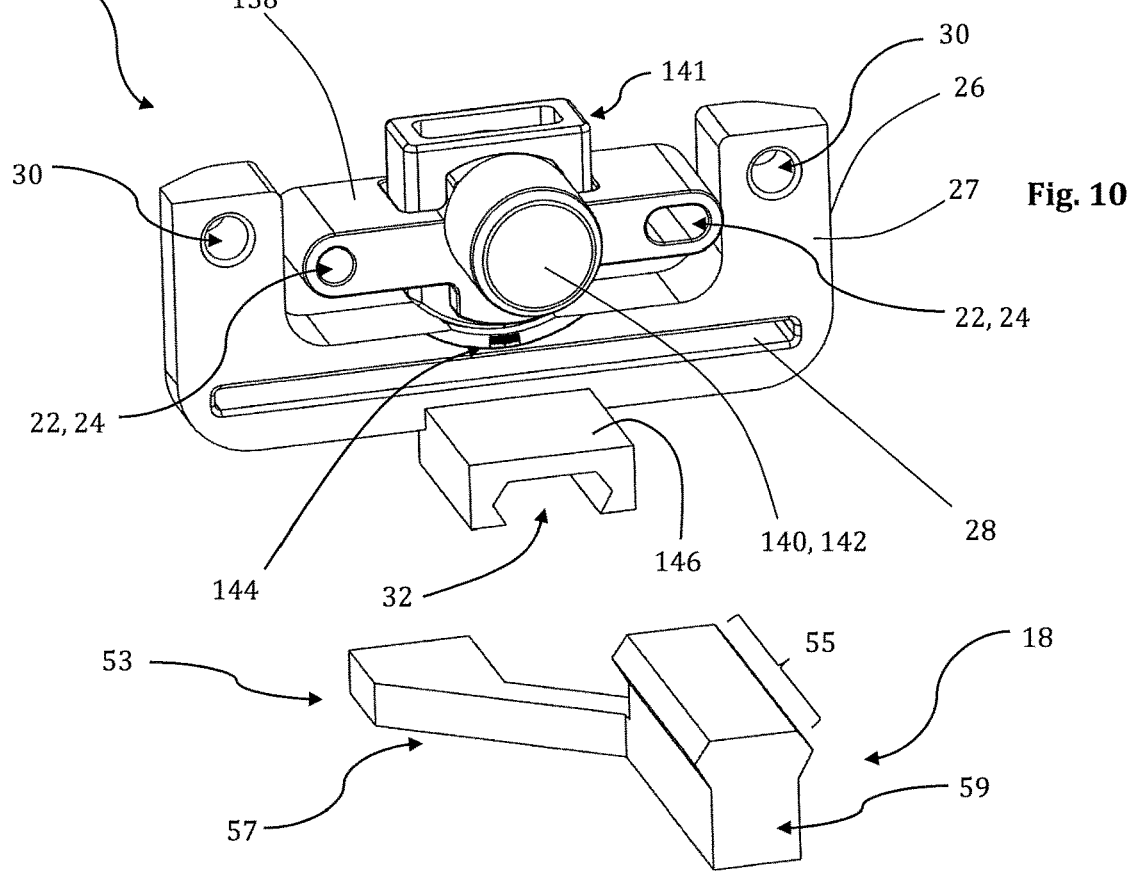
FIG. 10 is a perspective view of a distal femoral cutting block, which includes a block attachment solution to facilitate attachment of a connecting element to the block, the connecting element also shown.
Figure 11:
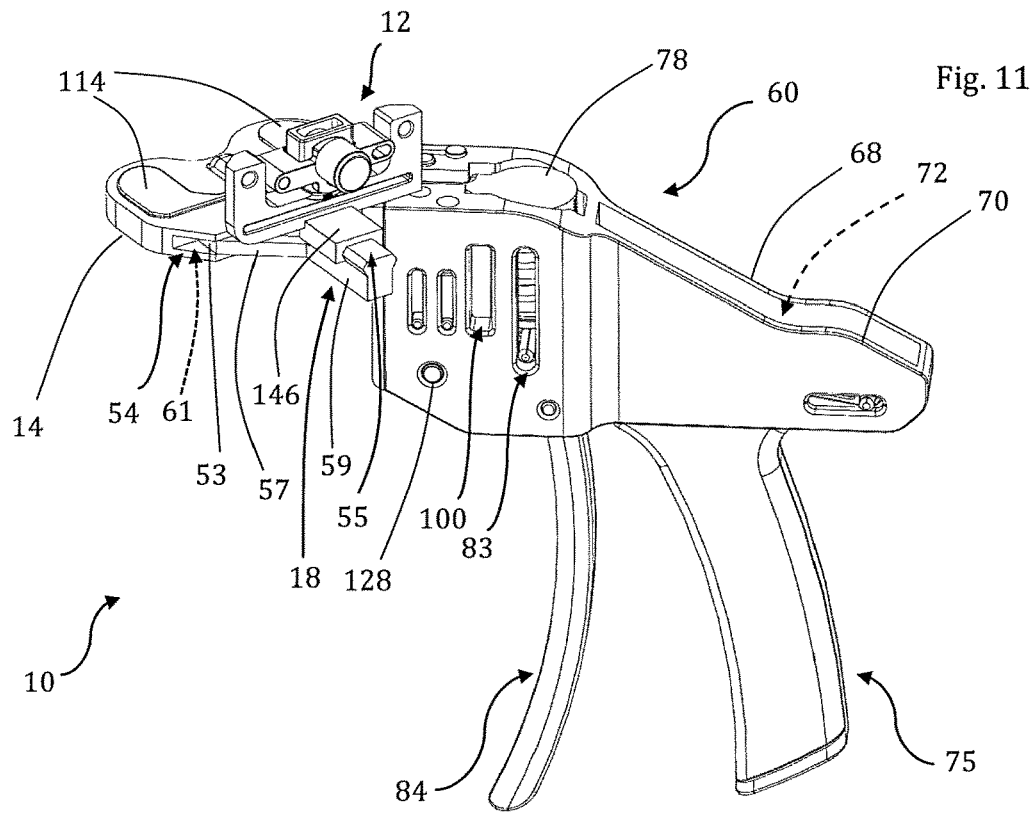
FIG. 11 is a perspective view of the device wherein there is attached the distal femoral cutting block of FIG. 10.

Such a connecting element 18 for connecting into the receiving port 54 of the tibial base plate 14 is shown with a distal femoral cutting block 12 in FIG. 10, wherein there is provided has a block attachment solution for attaching the connecting element 18 to the block 12 (Whether it be a distal femoral cutting block 12 or a femoral rotation block 13). The connecting element 18 has a protrusion 55 that is received by a receiving port 32 in the block 12, 13 (Thus there is provided a block attachment solution for attaching the connecting element to the block 12, 13). (Other attachment method(s) may be used). Thus in the shown example of FIG. 10, there is a male-female block attachment solution (male protrusion 55 from connecting element 18, female receiving port 32 on the block 12, 13). However, a female-male attachment solution may be provided, or any other block attachment solution, as is similarly the case for any plate attachment solution for connecting to the connecting element 18 to the base plate 14.

In the shown example of FIG. 10, the connecting element 18 is attachable to the tibial base plate 14 via a plate attachment solution 54, which is preferably provided by way of a protrusion 53 from the connecting element 18 that is received by the receiving port 54 in the base plate 14, (although any attachment method may be used). The protrusion 53 of the connecting element 18, in the example of FIG. 10, has an extending arm 57. It further comprises an intermediary section 59. Preferably the connecting element is dimensioned so that, when block 12 is attached to base plate 14, the cutting slot 28 of the block is appropriately distanced from the tibial base plate/tibial cut to facilitate desired resection of the femur 300—for example, the connecting element 18 may be dimensioned so that the cutting slot is distanced 20 mm above the tibial cut if 20 mm is the distance desired between femoral resection cut and tibial cut. This distance may differ dependent on what prosthesis is used in the gap.

In the embodiment of a connecting element 18 as shown in FIG. 1, FIG. 3, and FIG. 4, the connecting element 18 is a frame.

(The distal femoral cutting block 12 of FIG. 10 will be described in greater detail shortly).

The plate attachment solution 54 (which in the shown example comprises a receiving port 54 itself comprising a cavity 61) for receiving the protrusion(s) 53 of the connecting element 18 is configured in such a way that, once received into the receiving port 54, the connecting element 18 is movable and/or slidable (ie can slide) within the cavity 61 of the receiving port 54. Thus the block 12, 13' (when attached to the tibial base plate 14 via the connecting element 18 in such an embodiment) is also movable. Thus the distal femoral cutting block 12 is movably attachable to the tibial base plate via the connecting element. Thus, the distal femoral cutting block is slidable when engaged and/or connected to the tibial base plate in such an embodiment.

Thus the knee ligament tensioning and gap measuring device and the distal femoral cutting block 12 (or femoral rotation block 13) together form an instrument assembly for use in knee joint replacement surgery. (The knee ligament tensioning and gap measuring device may itself be provided by way of assembly, and/or kit of parts). The assembly including the distal femoral cutting block 12 of FIG. 10 is shown from various angles assembled in FIGS. 11 to 16 inclusive.

Figure 19:
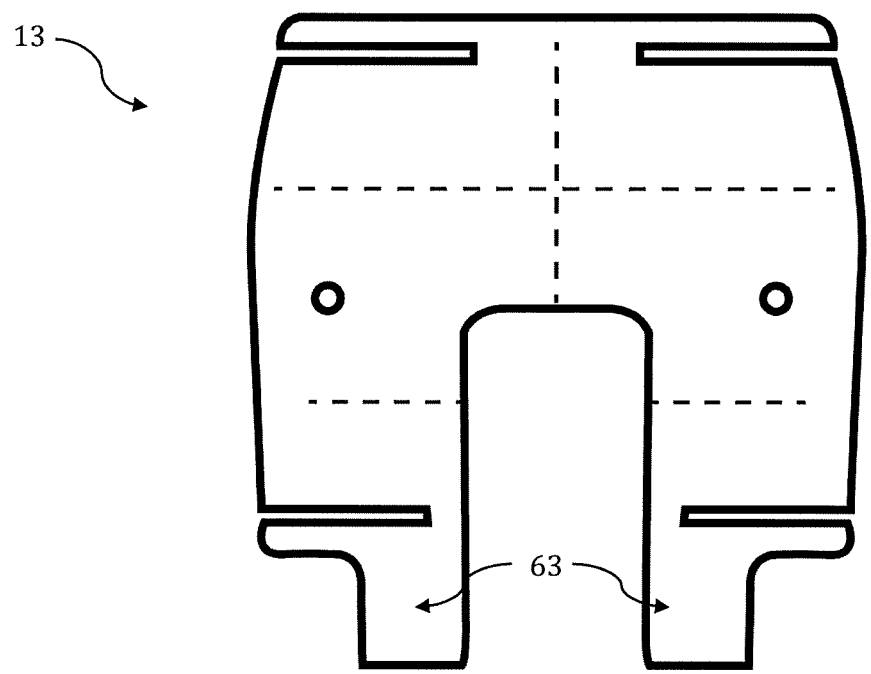
FIG. 19 is a femoral rotation block with an extended lower portion.
Figure 20:
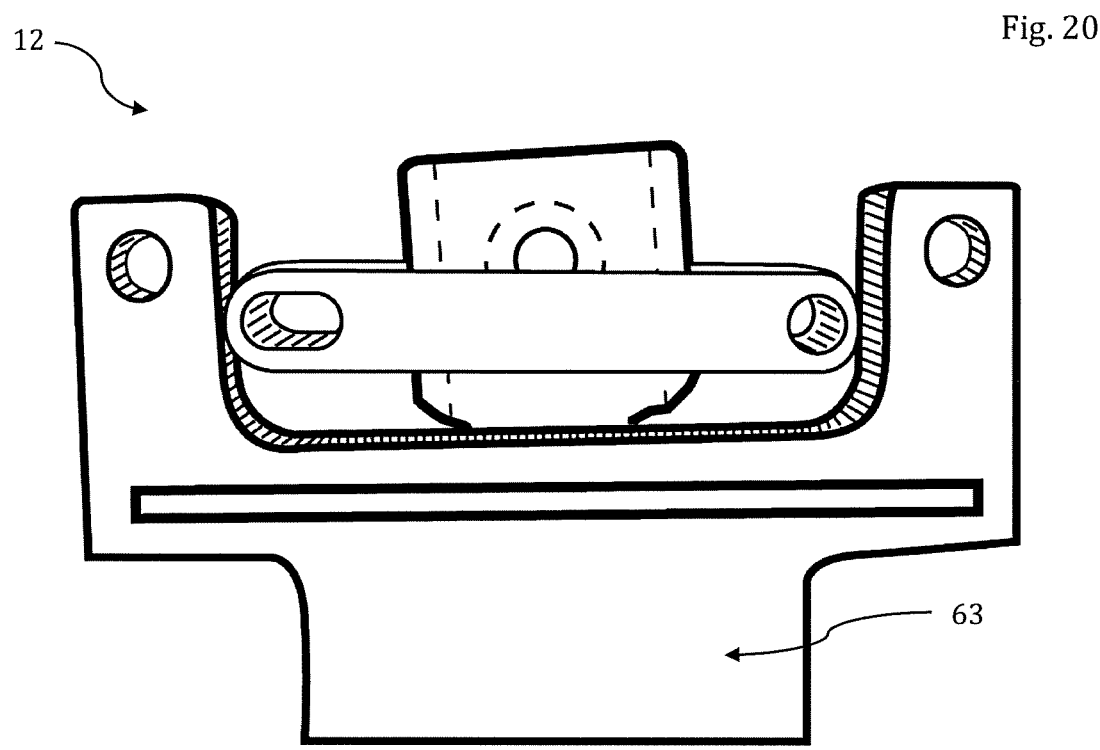
FIG. 20 is a back view of the example distal femoral cutting block with an extended lower portion.

Preferably this (attachment of the distal femoral cutting block 12) is achieved via the connecting element 18. However, it is feasible attachment of the cutting block 12 (or femoral block 13) is achieved without a connecting element 18. In such examples where attachment is achieved without a connecting element 18, the block 12, 13 may have an extended lower portion 63 to facilitate appropriate gap between cutting slot(s) of the block and tibial cut. Thus there is shown in FIG. 19 and FIG. 20 examples of a 4-in-1 cutting block 15 and distal femoral cutting block 12, wherein the blocks comprise an extended lower portion 63 to facilitate appropriate gap between cutting slot and tibial cut when the block 12, 13 are attached and/or engaged with the tibial base plate 14. In such an embodiment, preferably the (or a portion of) the extended lower portion 63 is magnetic, the block 12, 13 thus having a magnetic surface, or a portion of the tibial base plate 14 being magnetic to facilitate attachment.

Thus in this (or any) example, a magnetic solution may be provided for connecting block 12, 15 to base plate 14. In such an example, at least one of the tibial base plate 14 or the block 12, 15 have a magnetic surface.

In embodiments where no connecting element 18 is provided, any attachment solution not including a connecting element 18 may be provided. Pins, clips, screws, etc— any means for attachment may be provided.

In varying examples (in particular examples where no connecting element 18 is provided), the tibial base plate 14 may be extended (ie dimensioned) so that there is adequate space for the block 12, 13 to sit on, and engage with the base plate 14. A basic representation of this is shown in FIG. 19, where there is shown an extended plate portion 65 to create added surface area for engagement of the block 12, 13. The extended plate portion 65 is clearly shown as an extended rounded area (shown by way of example only, in no way limiting a scope of the term 'extended plate portion'). This may be particularly useful in, for example, embodiments that utilize a magnetic solution for attaching block 12, 13 to the tibial base plate.

It is intended that a 65 mm or 75 mm tibial base plate is used, although it is feasible any sized base plate 14 may be used. Base plates typically do not extend significantly (or at all) from tibial cut. Thus it will be extremely obvious if the plate is modified in this fashion to be extended and/or have an extended portion. Thus the tibial base plate, in such an example, may be extended on an anterior side and/or have an extended anterior portion.

In examples where no connecting element 18 is used for attachment (eg magnetic solution), such attachment solutions direct between block and tibial base plate may be referred to as 'direct attachment solutions', since the block is attachable to the base plate 14 directly, with no connecting element required.

There are obvious benefits in an attachment solution to attach the distal femoral cutting block or femoral rotation block to the tibial base plate. However, it is feasible no attachment solution is provided- and that the block simply 'rests' or is held on the tibial base plate for use.

It is feasible a connecting element may be used that is permanently attached to one or the other of the block or the tibial base plate. It is feasible that, rather than there being provided an extended lower portion on the block 12, 13 the base plate 14 may be extended upward and/or have an upwardly extending portion to create an appropriate gap when block 12, 13 and tibial base plate 14 are engaged.

Referring to the tensioning system, there is provided a means for tensioning the lateral and medial ligaments. Any means may be used. A tensioning 'system' need not be particularly complex and may simply comprise a means for tensioning lateral and medial ligaments. There are many ways to tension lateral and medial ligaments; for example- applying tension to the central rod of the femur when the knee is flexed; applying tension to the two pins (or any other drilled pins in the femur) that will take the distal femoral cutting block in extension; applying tension directly to the distal medial and lateral condyles; applying tension separately to the medial and lateral condyles from the tibial base plate; and applying tension to lower and upper leg—for example [eg pulling ankle outward and thigh upward, thus applying tension]; or by applying traction to the lower leg. These or any other methods for tensioning lateral and medial ligaments may be used, in no way limiting a scope of the present invention. However, in an example, as shown, there is provided a central tensioning element 33 as means for tensioning lateral and medial ligaments, which is a central limb 34.

The central tensioning element 33, 34 is configured to engage with, and apply pressure to, an intercondylar notch of the femur, thus tensioning lateral and medial ligaments. The central tensioning element 33 is a central limb 34.

It is feasible the means for tensioning lateral and medial ligaments is provided and/or carried out separately from the main body 60 of the knee ligament tensioning and gap measuring device. In such a case, the example may be described as a kit of parts, with a separate tensioning system used in tandem with the gap measuring system.

In the shown example, the top surface of the central limb 34 (or any central tensioning element 33) is rounded, forming a shaped (curved) head 38 to enable it to engage with the intercondylar notch whilst reducing any point-loading on the bone surface.

The central tensioning element 34, 33 comprises a protrusional arm 76, which stems from a tensioning element slide element 78 (which will herein be termed 'tension slide element' 78), the tensioning system thus further comprising the tension slide element 78. The tension slide element 78, in the shown example, is a vertical slide element, which can slide vertically up and down a tension slide barrel in the main body 60. Thus the central tensioning element 34, 33 can be adjusted in a vertical orientation via upward and downward sliding of the tension slide element 78. Thus the central tensioning element shaped head 38 is vertically adjustable up from the tibial base plate 14.

Figure 7:
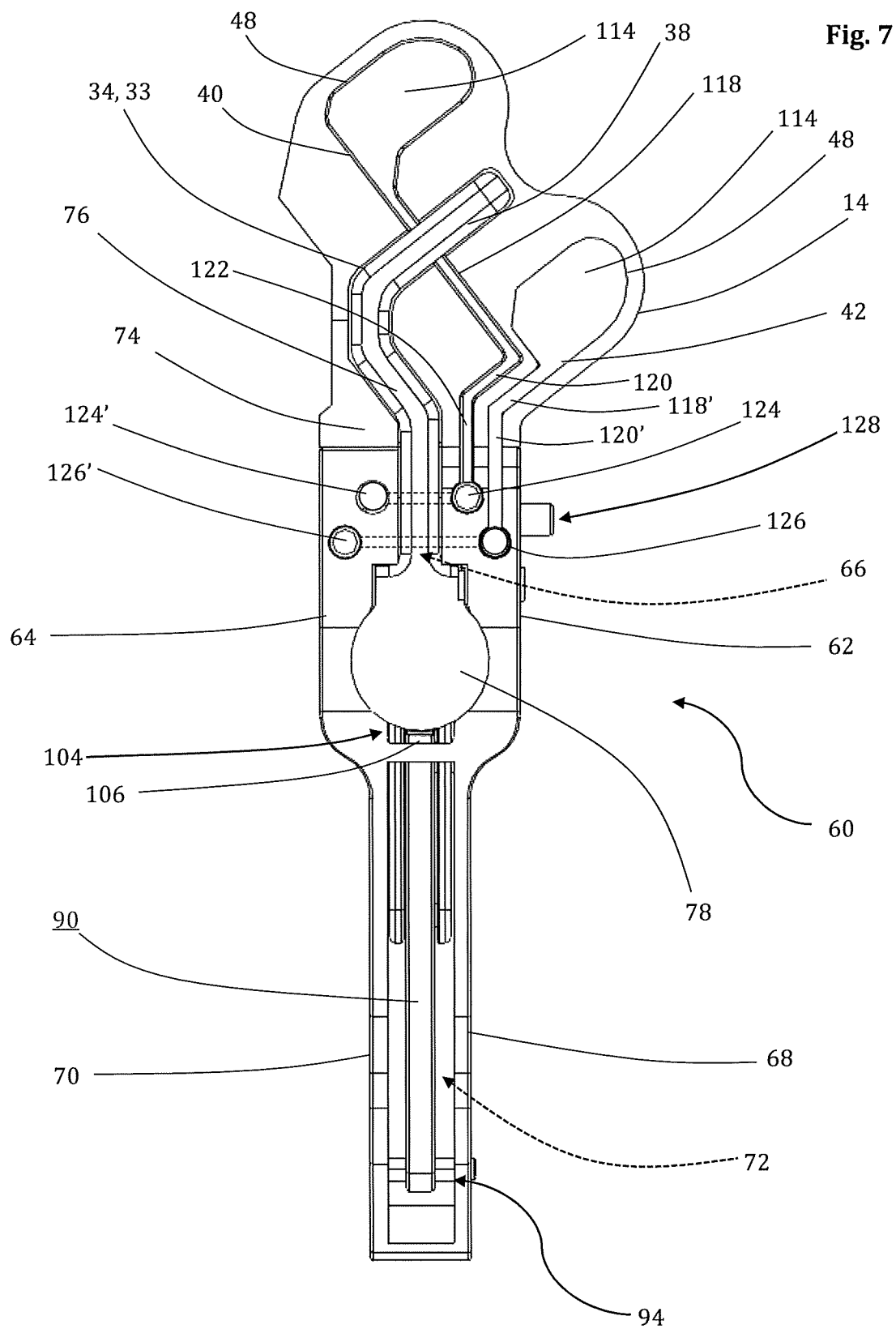
FIG. 7 is a top view of the device as shown in FIG. 6.

Shown best in FIG. 7, in the example, the protrusional arm 76 of the tensioning element 34, 33 is substantially kinked, or substantially L-shaped. The tensioning element protrusional arm 76 stems from the tension slide element 78 through the front central gap 66, with its head 38 taking up a substantially central position on (or about) the tibial base plate 14 to facilitate engagement with the intercondylar notch of the femur when vertically extended. In the preferred embodiment, there is a central recess 111 on the tibial base plate to house the central tensioning element head 38 when in a low position.

The tension slide element 78 is here shown as substantially cylindrical. However, it may be of any shape, size, dimension, etc. Housed within the tension slide element is a coil/spring 80 (which may be spring, etc and the like or any spring element). Thus the tension slide element 78 has a compression spring 80 that transmits the load (from a trigger mechanism) into the central limb 34, 33. Any means may be used as the spring element, not limited to being a coil, spring, etc and the like; for example, a resiliently flexible material may be used as the spring element, which need not be 'coiled' or look particularly 'spring-like' but may provide the spring function, and is thus termed a 'spring element'.

Thus in the shown example, the tensioning system further comprises a spring element, and more particularly preferably, comprises a compression spring 80 as the spring element. The spring 80 is preferably a significantly strong spring, as significant pressure may be required to tension lateral and medial ligaments. The spring 80 is viewable through a side aperture 82 (best shown in FIG. 8) in the tension slide element 78. There is provided a tension slide element slide aperture 83 which guides sliding of the tension slide element 78, which may be facilitated through use of a protruding slide pin 85. As the spring 80 compresses the relationship between the pin 85 and the top of the central limb 34, 33 reduces. The central limb 34, 33 therefore needs a slot aperture to allow this to happen.

The example vertically slidable tension slide element 78, in the example, can be vertically raised (or 'jacked/ratcheted') via a trigger 84, the tensioning system thus further comprising the trigger 84. This may be achieved in many ways. In the example, for example, (best shown in FIG. 9) the trigger 84 attaches to (or is integrally formed as part of) a first member 86 (internal members etc are shown in dashed lines to represent they are preferably housed within the device). There is provided a sliding pivot 88 (which may comprise a pivot pin 89) for the first member 86. When the trigger 84 is squeezed, the first member 86 is raised, which in turn raises a second member 90, which, as shown in the example embodiment, is preferably engaged with the first member 86 via a second sliding pivot 92 (which may comprise a second pivot pin 93). There is provided a back sliding pivot 94 (which may comprise a back pivot pin 95 and a back slide aperture 96 within which the back pivot pin 95 can slide) for the second member 90. The second member 90, at its opposing front end 91, is thus raised and engages with the tension vertical slide element 78, thus vertically raising the tension slide element 78. Thus the opposing front end 91 of the second member 90 has a relationship with the tension slide element 78 (whether it be engaging with, attached to, underneath the tension slide element 78, etc. Thus the (central) tensioning element 34, 33, which stems from the tension slide element 78, is raised, via squeezing of the trigger 84. This method is described by way of example only, and it will be obvious that there are many ways to raise the central limb/tensioning element 34, 33 via a trigger 84, or any other means, in no way limiting a scope of the invention. Thus the tensioning system may comprise any of the aforementioned elements.

It is feasible that a ratchet system may be employed, in which case, for example (best depicted in FIG. 9) there may be provided a row of teeth 97 on a (side) surface 98 of the tension slide element 78. A protruding element may thus be raised (or 'jacked/ratcheted') by squeezing of the trigger 84, which protruding element may then be caught and held within the ratchet teeth 97, thus allowing the tension slide element 78 to be jacked/ratcheted by squeezing the trigger 84 (or by any other means), wherein it is held, locked via locking of the protruding element(s) within the ratchet teeth 97. For this, or any other raising mechanism, there is preferably provided a release mechanism 100 to release the tension slide element 78. Any release mechanism 100 may be provided. For example, the release mechanism may be a catch release.

It may be beneficial for the user (surgeon) to know how much tension is being applied by the means for tensioning (which in the shown example is a central tensioning element 34, 33) and/or that pressure be limited within acceptable boundaries. It will be well known to those with skill in the art of such knee surgery that, in many quarters, it is deemed that a tension/pressure of approximately 200 Newtons should not be exceeded when tensioning the ligaments, otherwise it is feasible lateral and medial ligaments may rupture. (Such estimates are debated in various sectors of the industry).

Figure 15:
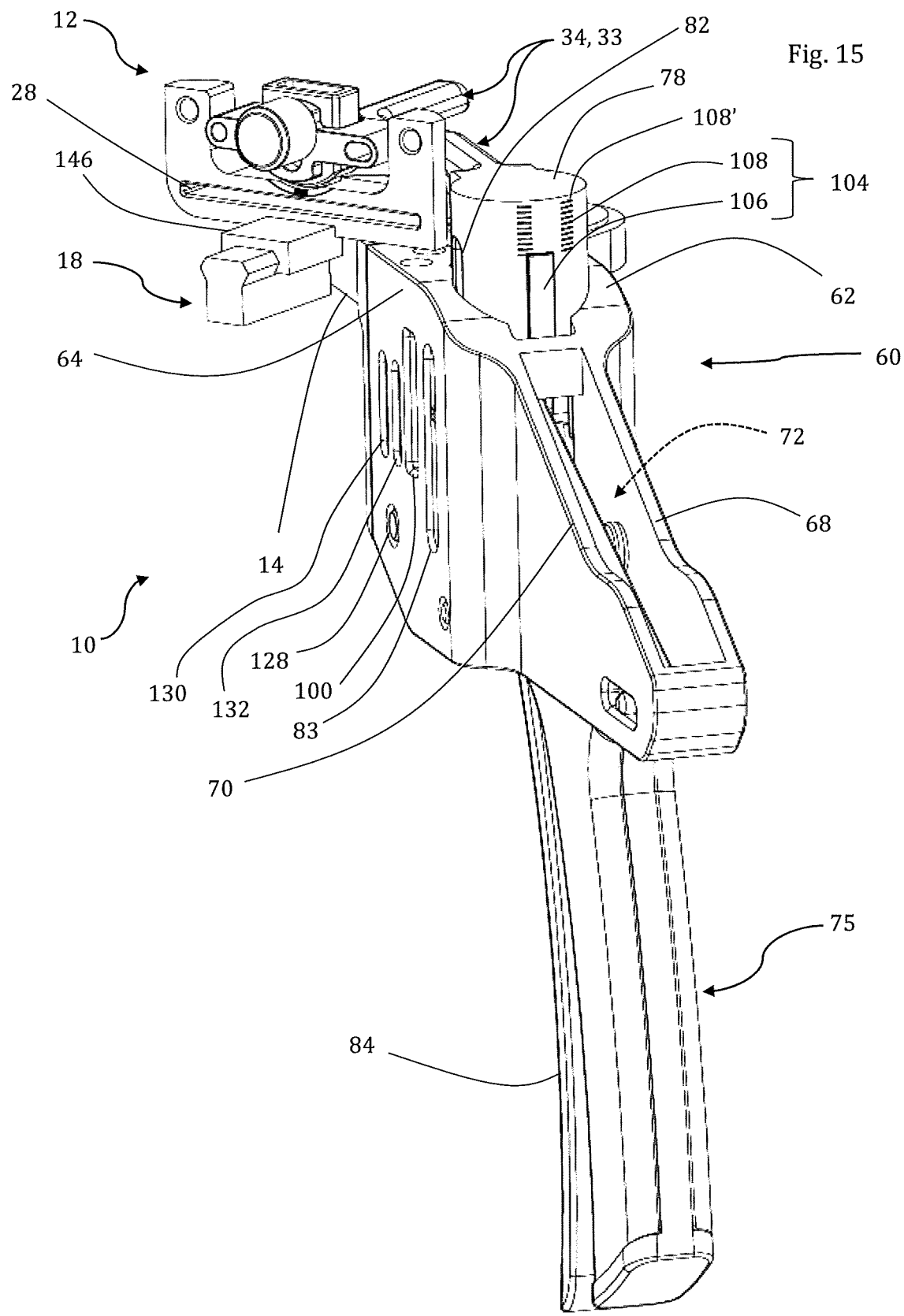
FIG. 15 is a back lateral perspective view of the assembly.
Figure 16:
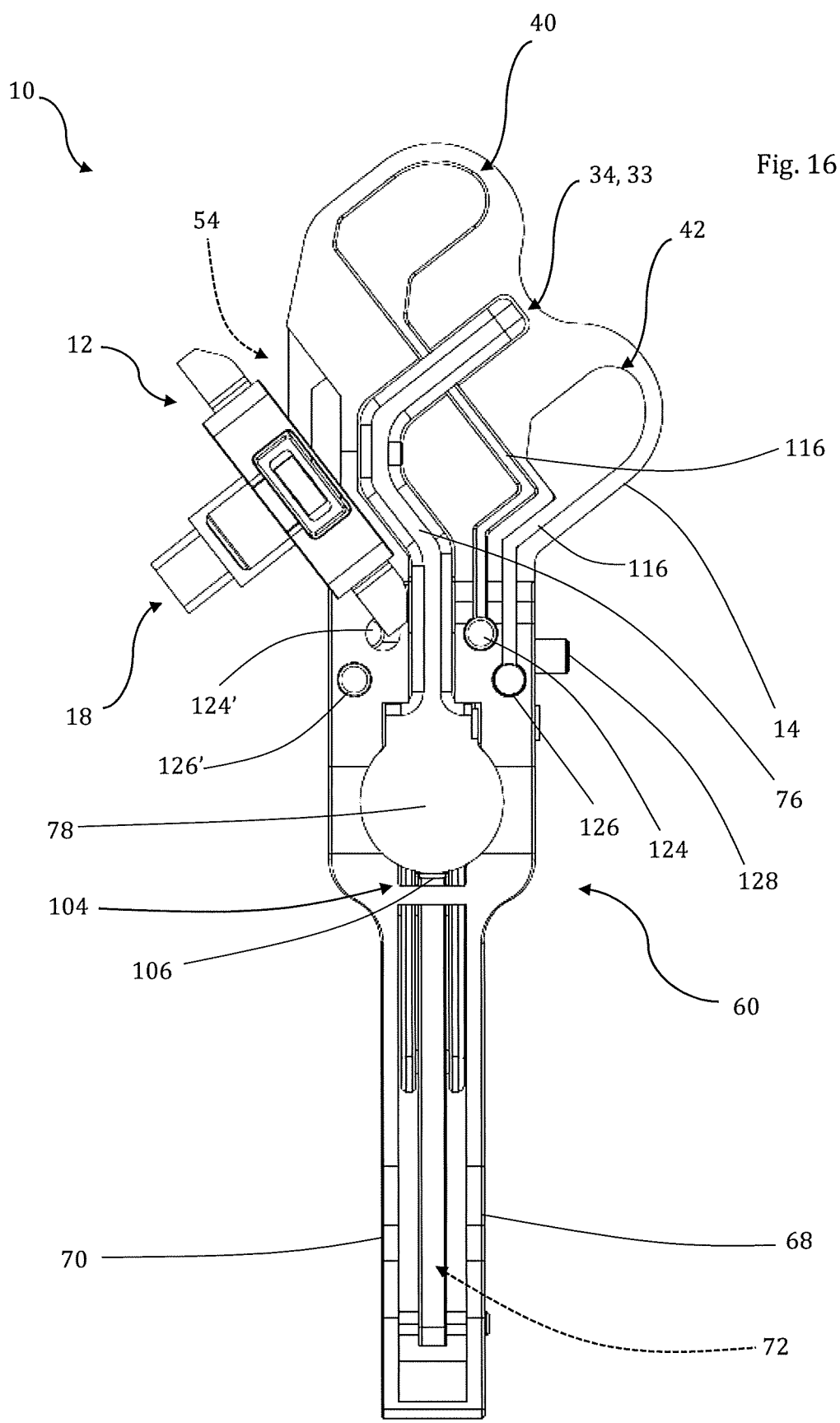
FIG. 16 is a top view of the assembly.
Figure 17:
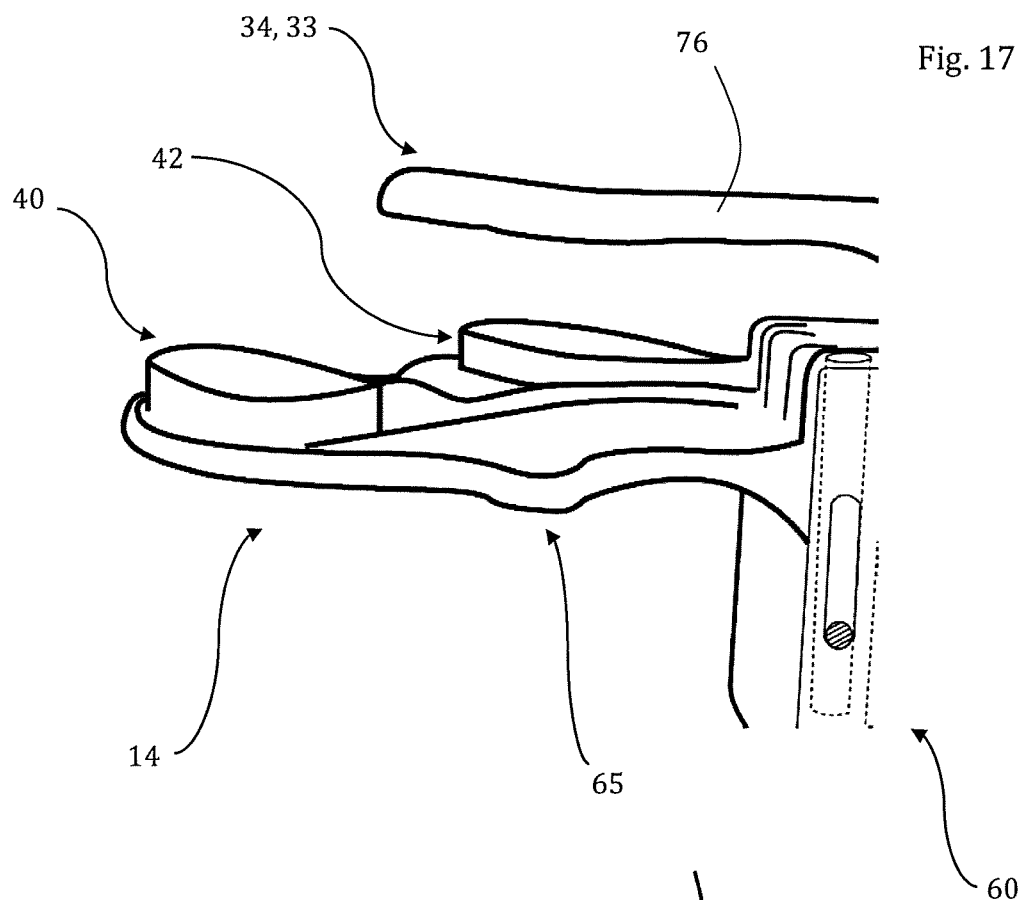
FIG. 17 shows an example of the device where the tibial base plate is extended, having an extended portion.

Thus there may be provided a tension reader 104 (best shown in FIG. 15). In the example of the shown drawings, the tension reader 104 is provided on a back portion of the tension vertical slide element 78 (but may be provided anywhere and by any means). The tension reader 104, in the shown example, comprises a reading element 106, and measurement indicators 108. (Indicators 108 may also be described as 'markings'). As more pressure is applied and the ligaments are further tensioned, the reading element 106 rises with respect to the indicators 108, the indicators thus showing how much pressure is being applied to the ligaments. Thus, for example, the top indicator 108' may be an indicator of 200 Newtons.

In the shown example, the spring element 80 transmits the load from the trigger mechanism to the central limb 33, 34. Thus the tensioning system allows the load applied to the central limb 34, 33 to be read on a scale (the tension reader 104); i.e. as the load applied through the trigger mechanism increases, the spring 80 is increasingly compressed. This change in spring compression is shown on the tension reader scale and is directly related to the load applied to the central limb 34, 33 and therefore the tension applied to the tendons. This allows load/tension to be communicated to the user (surgeon). The reading is (preferably) the force in Newtons applied between the base plate and the intercondylar notch. This force is the same as the tension applied to the ligaments.

In an example, the mechanism uses the central compression spring 80 to control the load applied, which in the preferred embodiment needs over 200 Newtons to fully compress it.

If the surgeon applies excessive load, the spring may completely compress and excessive load may be transmitted directly to the ligaments with damaging results. To diminish likelihood of this, the example may solely rely on the reading element 106 going off the scale, (thus communicating to a user that excessive tension is being applied) and the tension reader showing 104 protruding above a top of the central limb 34,33 and/or tension slide element 78 when this happens, (as well as the direct sense of feel that the surgeon will have for the load he is applying). In alternate examples, there may be provided a tension limiting system, such as, for example, a clutch mechanism to prevent excessive load being applied through the mechanism to the ligaments. Thus the tensioning system may further comprise not only the tension reader, but may also further comprise a tension limiting system/mechanism.

The scale with indicators 108 in the shown example is provided by way of example only, and any indicating means may be provided—for example, and not limited to, digital means, computer means, etc.

Figure 6:
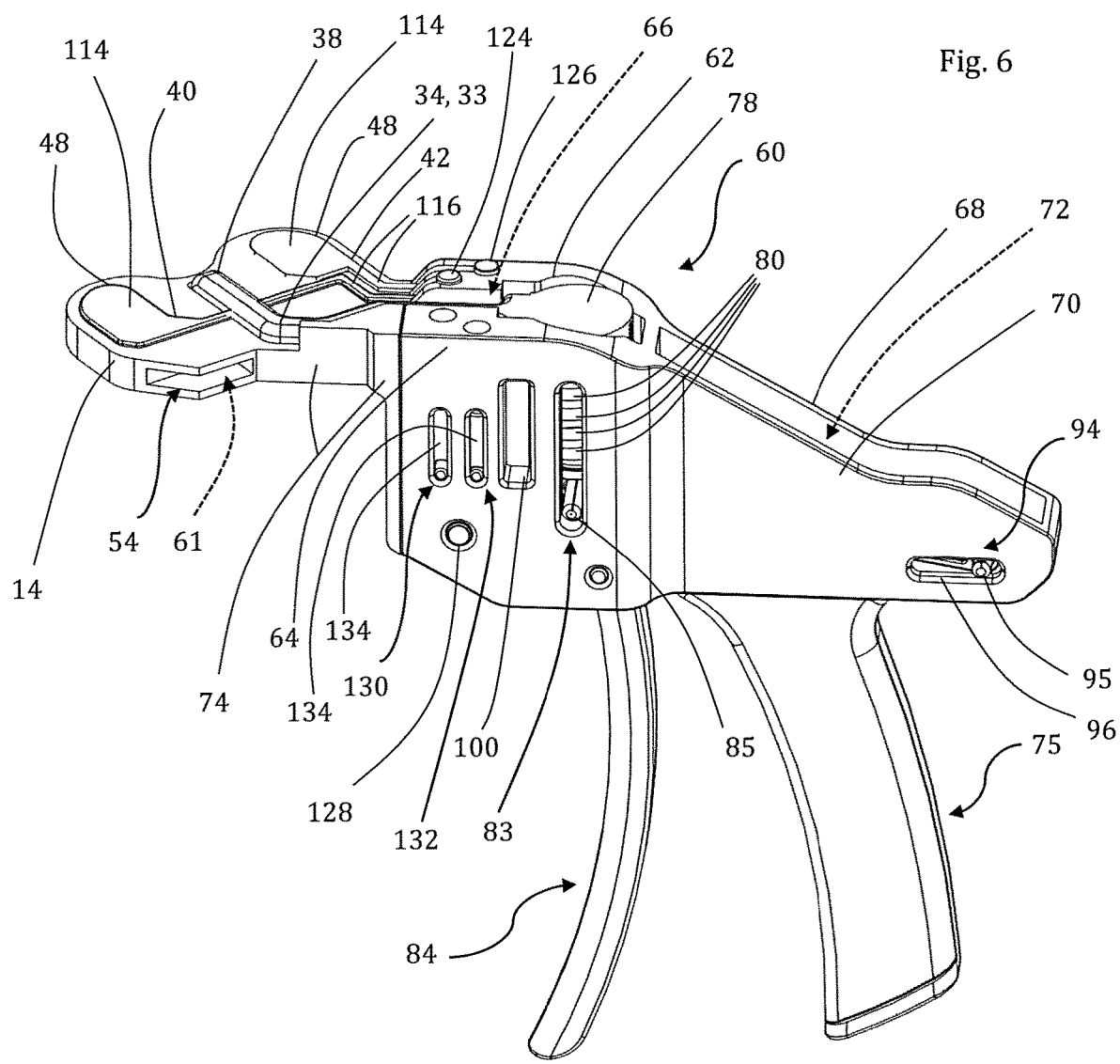
FIG. 6 is a lateral side perspective view of an example of a knee ligament tensioning and gap measuring device, wherein there is provided a main body for the device, with a tensioning element and gap measuring elements recessed.
Figure 8:
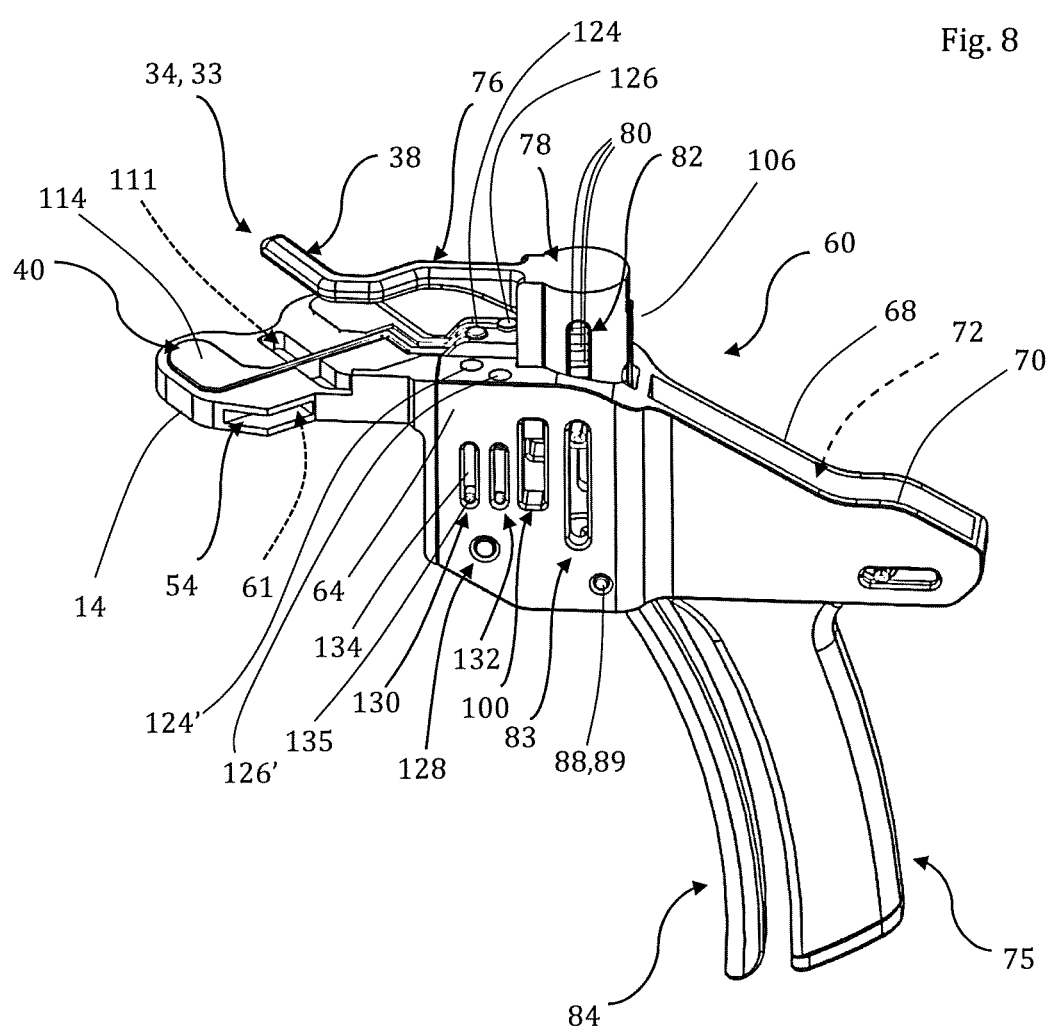
FIG. 8 is a lateral side perspective view of the example as shown in FIG. 6 and FIG. 7, wherein a central tensioning element is raised.

With respect to the measuring system, there is provided means for engaging lateral condyle and medial condyle of the femur, which, in the example as shown, is provided by way of a lateral gap measuring element 40 for measuring lateral gap (between lateral condyle and tibial cut) and a medial gap measuring element 42 for measuring medial gap (between medial condyle and tibial cut). The gap measuring elements 40, 42 preferably have shaped heads 48 for engagement with the condyles. The shaped heads 48 are shown in FIG. 6 recessed in the tibial base plate 14, the tibial base plate having a lateral recess 110 and a medial recess 112 for lateral and medial shaped heads 48. (The lateral recess 110 and medial recess 112 in the tibial base plate 14 are best shown in FIG. 8, where the gap measuring elements 48 are shown vertically raised from the tibial base plate 14).

The shaped heads 48 are shown having an engagement surface 114 for engaging a condyle. The engagement surfaces 114, in the shown example, are substantially flat which may be beneficial to more accurately and/or reliably measure gaps. Such a shape for the engagement surface/shaped head may also be beneficial in guaranteeing lowest point of the condyle is engaged.

The gap measuring elements 40, 42, in the shown example, comprise protrusional arms 116, which are substantially diagonal in shape. In the example, the lateral gap measuring element comprises (best shown from top view in FIG. 7) a first portion 118, a second portion 120, and a third portion 122, which stems from a slide element. The medial gap measuring element 42, in the shown example, simply comprises a first portion 118' and a second portion 120' which stems from a slide element. The portions (and thus the protrusional arms 116) are preferably formed as one part.

The protrusional arm 116 of the lateral gap measuring element 40 stems from a lateral gap measuring element slide element 124 (which will herein be termed the 'lateral slide element' 124). The protrusional arm 116 of the medial gap measuring element 42 stems from a medial gap measuring element slide element 126 (which will herein be termed the 'medial slide element' 126). Both lateral and medial slide elements 124, 126 are vertical slide elements, and can slide vertically within a vertical barrel in the main body 60, substantially similarly as the tension slide element 78 can slide vertically within a vertical (central) barrel in the main body 60.

It is feasible, in alternate examples, that there may be provided slide elements that do not slide vertically, but nevertheless, by various mechanical means, facilitate vertical adjustment of the gap measuring elements 40, 42 and/or tensioning element 33, 34. However, in the shown example, the barrels of the lateral and medial slide elements 124, 126 and of the tension slide element 78 are vertically oriented, and the slide elements are all vertical slide elements.

The vertical lateral and medial slide elements 124, 126 (best shown in FIG. 9 where the slide elements 124, 126 and gap measuring elements 40, 42 are shown raised) are substantially cylindrical in shape, as is the vertical barrel they slide through. However, similar to tension slide element 78 and tension slide barrel, they may be of any shape, size, dimensions, etc.

Best shown in FIG. 7, the lateral and medial slide elements 124, 126 and the slide barrels they slide through are shown in the example embodiment on the front first side 62 of the main body 60. There is shown a release mechanism 128 for releasing the gap measuring elements 40, 42, which in the shown example is a release catch 128 which protrudes from one side of the main body 60 to the other. The gap measuring elements 40, 42 are held in their lowest position by the release catch 128. In the example, when the catch 128 is released, the two gap measuring elements 40, 42 rise up, independently from each other, by means of a spring element (preferably a compression spring) applying a light upward load to each gap measuring element 40, 42. Intent is that the gap measuring elements remain engaged with the lowest point of each condyle. To re-set the gap measuring elements 40, 42 before next use they are manually pushed down and the catch 128 (or any release/catch mechanism 128) is re-engaged.

Again, best shown in FIG. 7, in the example, and shown by way of example only, there is shown a corresponding lateral slide element 124' on the front second side 64 of the main body, corresponding to the lateral slide element 124. There is also shown a corresponding medial slide element 126' on the front second side 64 of the main body 60, corresponding to the medial slide element 126. In the example, preferably the lateral vertical slide element 124 and the corresponding lateral slide element 124' are connected via a transverse connection. This may be achieved via a connecting member (or any other means/element), which is represented by way of example in FIG. 7 by dashed lines that transversely connect lateral slide element 124 to its corresponding lateral slide element 124'. Similarly, preferably the medial vertical slide element 126 and the corresponding medial slide element 126' are connected via a transverse connection (which may comprise a connecting member (or any other means/element).

Thus when the lateral and medial slide elements 124, 126 slide vertically in their barrels, raising (and lowering) the gap measuring elements 40, 42, so the corresponding lateral and medial slide elements 124', 126' correspondingly slide up and down their corresponding barrels. The fact that the slide elements 124, 126 have corresponding slide elements 124' and 126' improves the stability of the gap measuring platforms. However, such a configuration is provided by way of example only.

The corresponding lateral and medial slide elements 124', 126' may be substantially 'stubby' (ie abbreviated in length) in comparison to the lateral and medial slide elements 124, 126. Therefore whilst, as shown in FIG. 9, the lateral and medial slide elements 124, 126 may protrude significantly from their barrels when the lateral and medial gap measuring elements 40, 42 are raised vertically from the tibial base plate 14, their corresponding lateral and medial slide elements 124', 126' need not necessarily protrude from their barrels when the gap measuring elements 40, 42 are raised. It will be obvious to those with skill in the art that such a configuration is given and shown by way of example only.

With reference to FIG. 9 (and a plurality of other Figures), there are shown independent gap measurement readers for lateral and medial gaps, there being provided a lateral gap measurement reader 130 and a medial gap measurement reader 132. Thus, in the shown example, the measuring system comprises a gap measurement reader, and more preferably, comprises an independent lateral gap measurement reader 130, and medial gap measurement reader 132.

Each reader, in the shown example, comprises a gap reader aperture 134, and a gap reader element 135 (which in the shown example is a pin, post, etc or the like). Preferably there are (millimeter) measurement markings next to the gap reader aperture 134.

The pin could have a (horizontal) line in the middle so that it is clear to a user via the line in the pin what measurement is being read. A pin is shown by way of example only. In the example embodiment, the pin, post etc is connected to the corresponding lateral and medial vertical side elements 124', 126'. However, there may be a substantially similar (or the same) lateral gap measurement reader and medial gap measurement reader 132 on the first side 62 of the device. Thus there is also shown lateral gap measurement reader 130 and medial gap measurement reader 132 on the medial side view of the device of FIG. 13. There may be provided measurement indicators to communicate gap measurement to a user (surgeon, etc). Thus the readers 130, 132 may appear on both lateral and medial sides to allow the reading to be made on either side. It is feasible the main body may be symmetrical for use in both left and right handed versions. Such a version may be a universal main body version.

Under the corresponding slide elements 124', 126' (and lateral/medial slide elements 124, 126 on the first side 62 of the device) is provided a spring element(s) 136 (which is preferably a compression spring(s), although any element/compression material for applying upward force may be used; for example, feasibly a resilient sponge material may be used—any such element is a spring element). When catch 128 is pushed the medial and lateral gap measuring springs 136 get unloaded and are free to expand to measure the gaps on the medial and lateral side. This is carried out when the central limb 34, 33 has started to distract the knee. As soon as certain tension is applied and the medial and the lateral femoral condyles start rising from the tibial base plate, catch 128 can be pressed causing the lateral and medial measuring elements 40, 42 to touch the under surface of medial and lateral femoral condyles. Measurement is then readable on a first side 62 and second side 64.

Figure 12:
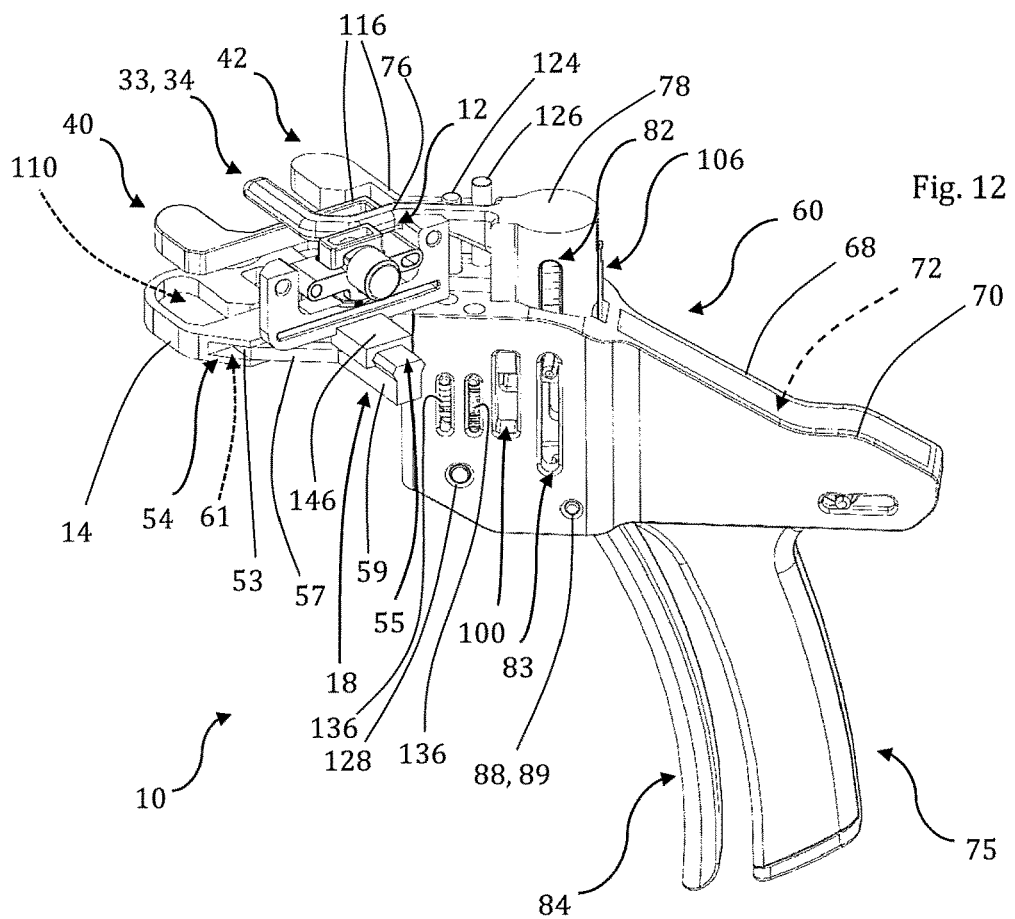
FIG. 12 is a same perspective view of the assembly of FIG. 11 with tensioning element and gap measuring elements raised.
Figure 13:
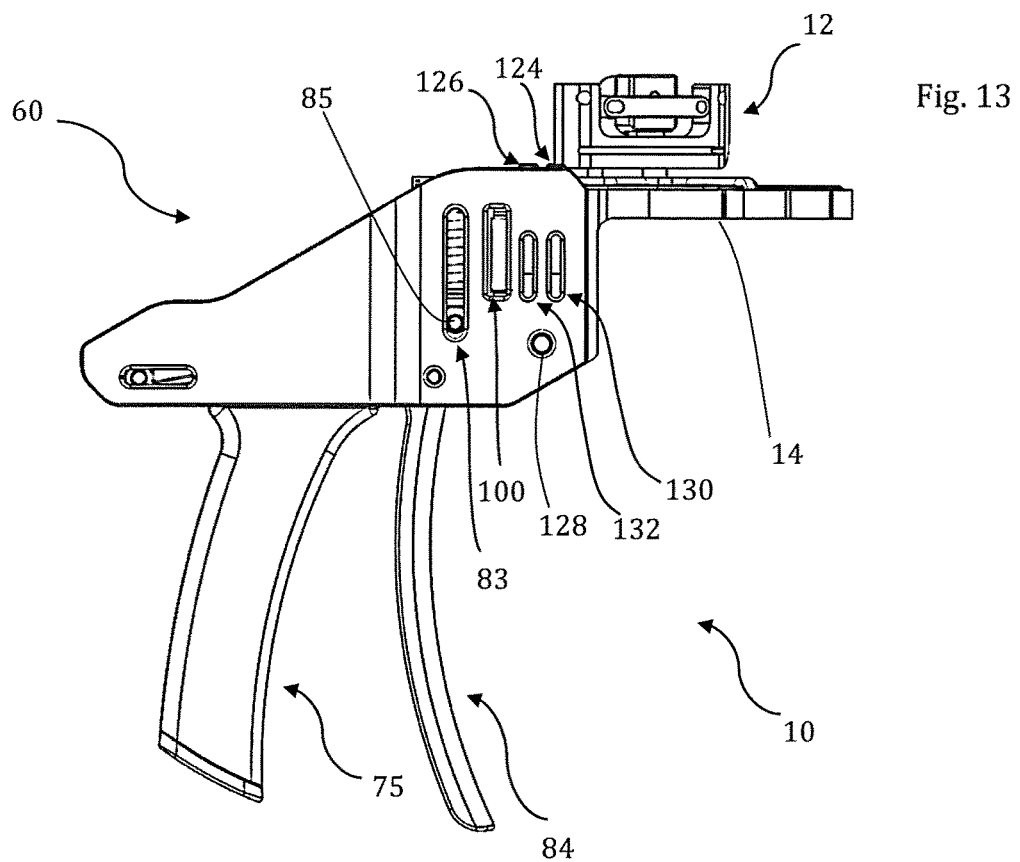
FIG. 13 is a medial side view of the assembly.
Figure 14:
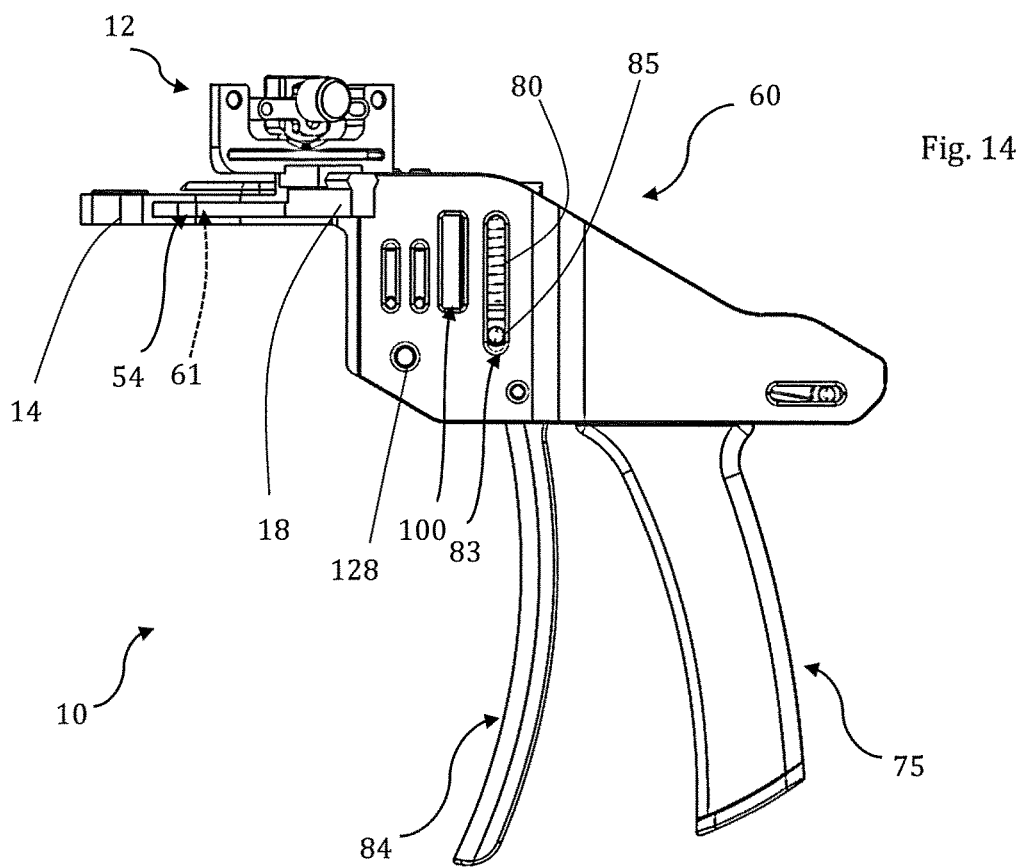
FIG. 14 is a lateral side view of the assembly.

Thus the gap measuring elements 40, 42 (via the lateral and medial slide element 124, 126 and their corresponding slide elements 124', 126') are locked, by default, in their low position (as shown, for example, in FIG. 12, where the shaped heads 48 of the gap measuring elements 40, 42 are recessed in the tibial base plate 14). When locked in such a position, the spring elements 136 are compressed and exert a (preferably substantially weak) force from underneath the slide elements 124, 126 and corresponding slide elements 124', 126'. Thus, when the release mechanism 128 is used, the corresponding slide elements 124', 126' are forced upwards by the spring element(s) 136, thus in turn forcing the lateral and medial slide elements 124, 126 vertically upwards, preferably via a transverse connecting element that connects the lateral and medial slide elements 124, 126 with their corresponding lateral and medial slide elements 124', 126'. This in turn springs the lateral and medial gap measuring elements 40, 42 vertically upwards from the tibial base plate 14 to engage with lateral and medial condyles respectively. (In alternate examples, it is feasible that a transverse connecting element is not needed, there being provided spring(s) (on the first side 62) for the lateral and medial slide elements 124, 126).

Thus when the lateral gap measuring element 40 engages the lateral condyle (such as via the lateral shaped head), the lateral reader element 135 is stopped in the lateral gap measurement aperture 134. There may be measurement indicators and/or markings on the (lateral) gap measurements reader(s) so that lateral gap measurement is communicated and/or can be read by the user (surgeon, etc). Similarly, medial gap can be communicated to and/or read by the user (surgeon, etc). Thus, in such an example, the device provides independent measuring of lateral and medial gaps when tensioned by the tensioning system. Any indication means may be provided; for example, digital, computer means, etc.

This method and/or means for how to raise/lower gap measuring elements 40, 42 and/or measure and communicate lateral and medial gaps is provided by way of example only, in no way limiting a scope of the invention.

Thus in the shown example, (where there is provided a main body, etc), the gap measuring elements and central limb are connected/attached or attachable to the tibial base plate via the main body, from which they stem.

It is feasible, in a varying example of the device, that there may be provided, rather than two separate lateral and medial gap measuring elements 40, 42, just one member which seesaws in contact between both condyles, the one member having a (lateral) engagement surface 114 for engaging a lateral condyle, and a (medial) engagement surface 114 for engaging a medial condyle. In such an example, therefore, the measuring system nevertheless comprises a lateral engagement surface 114 for engaging a lateral condyle, and a medial engagement surface 114 for engaging a medial condyle.

Figure 18:
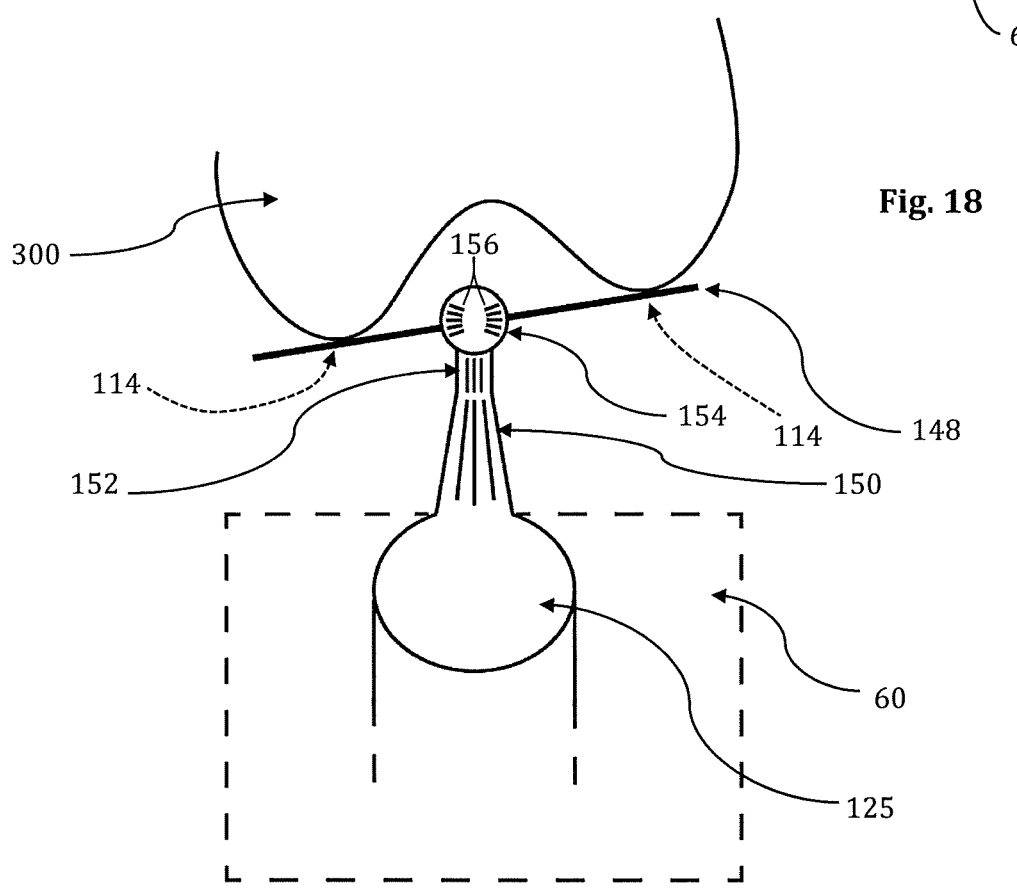
FIG. 18 is a basic representation of an example of a device wherein there is provided a seesaw element for engaging lateral and medial condyles.

Thus there is shown such an example in FIG. 18. The drawing is shown by way of representation alone. There is shown a means for engaging lateral and medial condyles, the means comprising a seesaw element 148 which has a lateral engagement surface 114 for engaging lateral condyle and medial engagement surface 114 for engaging medial condyle. There is provided a protrusional arm 150, which stems from a main body 60 (which may have a handle, etc) via a slide element 125', which (vertical) slide element 125' may facilitate vertical upward and downward adjustment of the protrusional arm 150, and thus of the means for engaging lateral and medial condyles.

In the example, at the end of the protrusional arm 150 (which may, for example, be substantially horizontal), there is a substantially vertical upward portion 152. On or about the portion is a dial 154. The dial 154 has indicators/markings 156, which may indicate degrees of orientation. Behind the dial 154 is the seesaw element 148, which is engaging both lateral and medial condyles. A means for tensioning the ligaments is preferably provided so that the ligaments are tensioned when the seesaw element is used as shown in FIG. 18. The slide element 125' shown is of significant size. However, it may be of any size, shape dimension, etc, and may, for example, be of similar size, dimension, function, etc to the lateral and medial slide elements 124, 124', 126, 126' as hereinbefore described. It is shown substantially centrally on the main body 60, but may be provided anywhere about the main body (or even in an embodiment where there is not provided a main body).

The slide element 125' (and thus the means for engaging lateral and medial condyles) may be releasable similarly to the lateral and medial gap measuring element 40, 42 as hereinbefore described, with all other feasible modifications and/or optional features as hereinbefore described. The seesaw element 148 may have specially shaped surfaces adapted for engagement with the condyles.

It is feasible other examples may be provided wherein each 'side' of the seesaw is independently upwardly and downwardly (and/or rotatably) movable in order to engage a condyle.

The dial 154, with its indicators/markings 156, may aid a user (surgeon, etc) in balancing the ligaments prior to resection of the femur 300.

Such an example may create a more complex interrelationship, measuring the 'average height' in the centre of the see-saw 148 and then having two additional and separate measurements for the individual condyles in relation to this 'average'. An important measurement is the amount of bone that will be removed from each condyle when the 20 mm gap (or whatever gap measurement is desired) is attained.

Markings and/or indicators on any element or feature may be provided electronically, mechanically, via computer, navigation, or any other method/means, etc.

Referring to the distal femoral cutting block 12, the cutting block 12 of FIG. 2 may lack appropriate modifications to more beneficially facilitate vertical adjustment and rotation of the cutting slot with reference to the femur. For example, it may be more beneficial to provide a distal femoral cutting block 12 comprising a vertical adjustment mechanism to facilitate vertical movement of the attachment means independent of the cutting slot (which may also be said to be vertical movement of the cutting slot independent of the attachment means).

In such a way, there is provided in FIG. 10 a distal femoral cutting block 12 which comprises a block body 26; a cutting slot 28; an attachment means for attaching the distal femoral cutting block 12 to a femur 300 that facilitates varus and valgus rotation; and a vertical adjustment mechanism to facilitate vertical movement of the attachment means independent of the cutting slot, the distal femoral cutting block thus configured to facilitate both varus and valgus rotation of the cutting slot and vertical adjustment of the cutting slot with reference to the femur.

The cutting block 12 comprises an attachment means for attaching the cutting block 12 to the femur. The attachment means need not be an aperture(s), but for the shown example does comprise a first rotation aperture 22, 24, and a second rotation aperture 22, 24, which, since they facilitate varus and valgus rotation of the block body 26/cutting slot 28 with reference to the femur 30, may each be termed varus/valgus rotation apertures 22, 24. The apertures (and thus the shown attachment means are configured to facilitate attachment of the cutting block (and thus placement of the cutting slot 28) to the femur via pins, which it is well known are commonly pinned into the femur 300 for attachment of such blocks. The apertures 22, 24 thus each receive a pin in such an example.

However, it will be obvious that there may be other ways to facilitate attachment (and thus other attachment means). For example, again for an example where the distal femoral cutting block is configured to receive pins, it is feasible, for example, that there may be provided an intermediary element that is placed on an end of the pins. This element may, for example, be circular, and have a rotatable portion. There may then be provided an attachment means on the cutting block 12 to 'clip' and/or attach to the intermediary element, thus attaching the cutting block rotatably. Thus it is shown the distal femoral cutting block is not limited to having apertures as the attachment means. And attachment means may be provided.

Furthermore, it is feasible other methods are used for attachment other than pins which are pinned into the femur. In such cases where element(s) other than two pins are used to facilitate attachment of the cutting block 12, an attachment means other than apertures may be provided. Furthermore even where pins are used on the femur, it is feasible they 'clip' and/or attach to the distal femoral cutting block, rather than requiring apertures. This it is clear that the attachment means for the distal femoral cutting block is not limited to being (or comprising) apertures.

In the shown example, however, the cutting block 12 comprises a block body 26, a cutting slot 28, a varus rotation aperture 22, 24 to facilitate attachment of the cutting block 12 to a femur 300 and to facilitate varus rotation of the cutting slot 28 with reference to the femur 300, a valgus rotation aperture 22, 24 to facilitate attachment of the cutting block 12 to a femur 300 and to facilitate valgus rotation of the cutting slot 28 with reference to the femur 300, and a vertical adjustment mechanism to facilitate vertical movement of the varus and valgus rotational apertures 22, 24 with reference to the cutting slot 28.

The varus and valgus rotation apertures, 22, 24 can thus be raised and lowered with respect to the cutting slot 28 (and thus the cut to the femur). Since the varus and valgus rotation apertures (or any attachment means) are effectively pinned to the femur in this embodiment, the vertical adjustment mechanism facilitates vertical movement of the cutting slot independent of the attachment means. One intent of the shown distal femoral cutting block is to divorce vertical movement from rotational movement. Thus a portion of the cutting block 14 is independently vertically adjustable and rotatable from a main block body 27 of the cutting block, which main block body 27 comprises the cutting slot. This facilitates vertical and rotational movement of the cutting slot 28 with reference to the femur 300, with the cutting block attached to the femur 300.

In the shown example, there is provided a rotatable element 138 for the varus and valgus rotation apertures 22, 24, wherein the varus and valgus rotation apertures 22, 24 are provided at opposing sides of a fulcrum of the rotatable element 138 (as shown in FIG. 10). Since the rotatable element 138 includes the varus and valgus rotation apertures 22, 24, varus and valgus rotation of the cut with reference to the femur 300 is thus facilitated via rotation of the rotatable element 138, which facilitates rotation of the cutting slot 28 with reference to the femur.

The rotatable element 138 is vertically adjustable in height from the cutting slot 28 via the vertical adjustment mechanism. Thus the cutting slot is vertically adjustable with reference to the femur 300.

Simply raising and lowering the height of the rotatable element 138 substantially manually may be inaccurate, and may not lock the height at a desired level. Thus there is provided an adjustment means 140 which facilitates accurate height adjustment of the rotatable element 138 (and/or the varus and valgus rotation apertures 22, 24), which allows height of the rotatable element 138 to be adjusted, and maintained. Preferably the adjustment means 140 is a dial 142, which is preferably a rotatable dial 142, as shown in FIG. 10.

There is shown a rotation measurement reader 144 underneath the dial 142 to communicate and display femoral rotation to a user (surgeon), which may comprise angle of rotation markings and/or indicator(s).

In the shown example, there is provided a block attachment solution for securely attaching a connecting element 18 to the distal femoral cutting block 12. The block attachment solution, in the shown example, comprises a receiving port 32, which receives a protrusion 55 of the connecting element 18. The block attachment solution further comprises a protruding portion 146.

One (or both) of the varus and valgus rotation apertures 22, 24, in the shown example, is slightly augmented in size. This allows for minor variances in distance between attachment pins received by the cutting block 12. Thus the right-sided varus/valgus rotation apertures 22, 24 in FIG. 10 is shown substantially lozenge-shaped (augmented in size). Any attachment means where such modification is apt may have such a modification (ie a modification to allow for variances in distance between attachment pins (or any other attachment element(s)).

The DFCB engages with the 2 pins already drilled into the femur (with one aperture augmented in size to one pin to allow for inaccuracies). The rotatable element 138 can move vertically, sliding vertically relative to the main block body 27, and thus relative to the cutting block 12. Thus the attachment means can move vertically relative to the cutting slot 28. The rotatable element is also rotatable relative to the cutting slot 18, rotatable with a movement facilitation element 141, (which in the shown example, connects the attachment means to the main block body 27), preferably up to 7 degrees.

There may be provided a rotation limitation means; thus one function for the movement facilitation element 141 in this example is to provide limits to the vertical movement and angular rotation to prevent the surgeon going beyond acceptable limits. This is achieved in the example simply by dimensioning of the movement facilitation element 141, which is dimensioned such that it meets a stop (which may be any part of the block), thus limiting at least one of: angular rotation; vertical movement, or both. Angular rotational may be limited to within appropriate parameters, such as between 3 and 7 degrees varusly and valgusly, or may be limited to particular values, such as 3, 5 and 7 degrees (varusly and valgusly).

The example apparatus described above can be used in a method for performing a knee replacement surgery, which includes some or all of the following steps: Opening the knee; Cutting the proximal surface of the tibia by traditional jig/navigation or patient specific jigs; Fixing the individual knee replacement specific distal femoral cutting block with 2 pins by traditional/navigation or patient specific means; Removing the company specific distal femoral cutting block but retaining the 2 pins which fixed the cutting block; Suspending loosely the tensioner distal femoral cutting block to the femur by means of the 2 pins that fixed the knee replacement specific distal femoral cutting block; placing the tensioner base plate on the cut tibial surface; fixing the tensioner distal cutting block to the tensioner baseplate by the tensioner fixing mechanism; Applying tension through the ratchets to the central tensioning element thereby tensing the medial and lateral collateral ligaments; Visualising the medial and the lateral gap measuring elements that will reflect the potential medial and lateral gap between the tibial cut surface and the potential femoral distal cut; Assessing the distal femoral cutting block on the tensioner tibial base plate which provides the change in varus/valgus angle of the potential distal femoral cut and proximal/distal movement of the potential distal femoral cut associated with tensioning of the central tensioning limb of the tensioner; Fixing the distal femoral cutting block to the femur with 2 or more additional pins once acceptable and usually 18-22 mm rectangular space can be acheived; Cutting the distal femur; measuring and confirming the standard gap between the proximal tibial cut and the distal femoral cut thereby confirming a rectangular extension gap between the tibial cut and distal femoral cut; removing the distal femoral cutting block and the ligament tensioner; bending the knee; placing the tibial baseplate of the tensioner on the cut tibial surface; placing the tensioning limb on the intercondylar notch; tensioning the ligaments using the ratchets on the tensioner thereby tensing the medial and lateral knee ligaments; placing the flexion cutting block securely on the tibial baseplate of the tensioner; assessing the medial and lateral gaps using the measuring elements; assessing the anterior cut of the femur to confirm there is no notching; assessing adequate medial and lateral posterior condylar cuts before the cuts are made; assessing the surgical and transepicondylar axis; assessing the whitesides line; drilling 2 horizontal holes to allow the company specific cutting block to cut the anterior/posterior and chamfer cuts of the femur; assessing and confirming that the flexion gaps are accurate by the gap measuring elements; correcting inaccuracies; Fixing the knee replacement specific cutting block; making the posterior femoral condylar cut; making the anterior femoral cut; making the chamfet femoral cuts; trialling the femoral and tibial implants with the plastic; assessing the implant stability and mobility; cementing the definitive femoral and tibial implants; assessing the balancing and patellar tracking; washing the knee; closing the knee.

A method of carrying out knee surgery will now be provided to further illustrate nature of the invention. Not all steps provided are essential. Steps are provided, where possible, in chronological order of execution, however, the following description of the method for carrying out knee surgery is not limited to being carried out in the chronological order as described. Thus there is provided:

A method for performing a knee replacement comprising:
Opening a knee;
Cutting a proximal surface of the tibia (preferably by traditional jig/navigation or patient specific jigs);
Fixing a (preferably individual knee replacement specific) distal femoral cutting block AND/OR DISTAL FEMORAL BLOCK (preferably with 2 pins, and preferably by traditional/navigation or patient specific means);
Removing a (preferably company specific) distal femoral cutting block AND/OR DISTAL FEMORAL BLOCK but retaining attachment means, (which is preferably 2 pins) which fixed the cutting block;
Suspending, preferably loosely, the distal femoral cutting block to the femur (preferably by means of the 2 pins (or any attachment means) that fixed the distal femoral cutting block (which is preferably a knee replacement specific cutting block and/or femoral block);
placing the tibial base plate on the cut tibial surface;
preferably fixing the distal cutting block and/or distal femoral block to the tibial base plate by a fixing mechanism (which is preferably a connecting element, but may include a mechanism such a magnetic mechanism, which may not include a separate connecting element);
Tensioning ligaments, preferably via applying tension, most preferably via a ratchet system, tension achieved preferably via tensioning a central tensioning element thereby tensioning the medial and lateral collateral ligaments;
Measuring medial and the lateral gap, preferably via medial and lateral gap measuring elements, which preferably engage the femur, and more preferably engage lateral and medial condyles, thus gauging the medial and lateral gap between the tibial cut surface and femoral distal cut;
Preferably assessing the distal femoral (cutting) block on the tibial base plate to check the block is positioned correctly;
Fixing the distal femoral (cutting) block to the femur (preferably with 2 or more additional pins);
measuring and confirming the gap between the proximal tibial cut and the distal femoral cut thereby confirming a rectangular, extension gap between the tibial cut and distal femoral cut;
Cutting the distal femur;

Preferably measuring the gap between proximal tibial cut and distal femoral cut, most preferably to confirm that the rectangular, gap has been achieved removing the assembly of the distal femoral cutting block and the ligament tensioning device. Furthermore, preferably the following steps are also carried out following the distal femoral cut:

bending the knee;

placing the tibial baseplate (which is preferably part of the tensioning device) on the cut tibial surface;

placing the tensioning element (which is preferably a central limb) on the intercondylar notch;

tensioning the ligaments, preferably using the ratchet system of the tensioning device (which preferably further comprises a main body) thereby tensioning the medial and lateral knee ligaments;

placing the flexion cutting block on the distal femur, preferably on a cut surface of the femur;

measuring the medial and lateral gaps using the gap measuring elements;

preferably assessing an anterior cut of the femur to confirm there is no notching;

preferably assessing medial and lateral posterior condylar cuts before the cuts are made to make sure that the flexion gap is rectangular, (or substantially rectangular);

preferably assessing surgical and transepicondylar axis;

preferably assessing the whitesides line;

preferably drilling 2 (or any number) of (preferably) horizontal holes in the femur to facilitate attachment of the (preferably company specific) cutting block to cut the anterior/posterior and chamfer cuts of the femur;

preferably assessing and confirming that flexion gaps are accurate, preferably by re-introduction the gap measuring elements;

correcting any inaccuracies if required;

Fixing the (preferably knee replacement specific) cutting block;

executing a posterior femoral condylar cut;

executing an anterior femoral cut;

executing a chamfer femoral cuts;

trialling the femoral and tibial implants, preferably with a plastic placer;

preferably assessing implant stability and mobility;

fixing definitive femoral and tibial implants, preferably via cementing;

preferably assessing ligament balancing and patellar tracking;

washing the knee;

closing the knee.

Preferably the distal femoral (cutting) block provides the change in varus/valgus angle of the potential distal femoral cut and proximal/distal movement of the potential distal femoral cut associated with tensioning of the central tensioning limb of the tensioner.

Preferably the distal femoral (cutting) block is fixed to the femur once acceptable and usually 18-22 mm rectangular space has be achieved.

The embodiments described above are provided by way of example only, and various other modifications will be apparent to persons skilled in the art without departing from the scope of the invention as defined by the appended claims.

The invention claimed is:

1. A ligament tensioning and gap measuring device, comprising:

a tibial base plate;

a tensioning arrangement comprising a central tensioning element configured to engage an intercondylar notch of a femur in use, upwardly applying pressure thereon to tension a lateral ligament and a medial ligament; and a measuring arrangement comprising:

a lateral gap measuring element for engaging a lateral condyle, the lateral gap measuring element being movably mounted relative to the tibial base plate;

a lateral gap measurement reader configured to measure a position of the lateral gap measuring element;

a medial gap measuring element for engaging a medial condyle, the medial gap measuring element being movably mounted relative to the tibial base plate; and a medial gap measurement reader configured to measure a position of the medial gap measuring element;

such that the measuring arrangement is configured to independently measure a lateral gap and a medial gap when the lateral and medial ligaments are tensioned by the central tensioning element.

2. A ligament tensioning and gap measuring device as claimed in claim 1, wherein the tibial base plate comprises an extended plate portion to create added surface area for engagement of a femoral block.

3. A ligament tensioning and gap measuring device as claimed in claim 1, wherein the tibial base plate comprises an attachment to facilitate attachment of a femoral block.

4. A ligament tensioning and gap measuring device as claimed in claim 3, wherein the attachment to facilitate attachment of the femoral block forms part of a direct attachment solution, wherein the femoral block is attachable directly to the tibial base plate.

5. A ligament tensioning and gap measuring device as claimed in claim 3, wherein the attachment to facilitate attachment of the femoral block forms part of an indirect attachment solution, wherein the femoral block is attachable indirectly to the tibial base plate, via a connecting element, the attachment to facilitate attachment of the femoral block being configured to facilitate attachment of the connecting element to the tibial base plate.

6. A ligament tensioning and gap measuring device as claimed in claim 5, wherein the attachment to facilitate attachment of the femoral block comprises a receiving port.

7. A ligament tensioning and gap measuring device as claimed in claim 1, wherein the device further comprises a main body.

8. A ligament tensioning and gap measuring device as claimed in claim 1, wherein the device further comprises a main body and wherein the lateral and medial gap measuring elements each comprise a vertical slide element, the main body comprising:

a barrel within which the vertical slide element of the lateral gap measuring element is vertically slidable; and a barrel within which the vertical slide element of the medial gap measuring element is vertically slidable.

9. A ligament tensioning and gap measuring device as claimed in claim 8, wherein the lateral gap measurement reader and the medial gap measurement reader are provided by way of the vertical slide elements of the gap measuring elements sliding up and down vertically to provide a measurement.

10. A ligament tensioning and gap measuring device as claimed in claim 9, wherein the gap measurement readers are provided at a side of the main body.

11. A ligament tensioning and gap measuring device as claimed in claim 9, wherein the lateral gap measurement reader comprises a gap reading element that slides up and down with the lateral gap measuring element and the medial gap measurement reader comprises a gap reading element that slides up and down with the medial gap measuring element, in order to provide a measurement reading.

12. A ligament tensioning and gap measuring device as claimed in claim 8, wherein the tensioning arrangement further comprises a vertical tension slide element, the main body further comprising a barrel within which the vertical tension slide element is vertically slidable.

13. A ligament tensioning and gap measuring device as claimed in claim 8, wherein the device comprises a handle, and user control to initiate tensioning of the lateral and medial ligaments, via the central tensioning element, provided in proximity to the handle, such that, in use, the device can be held, and ligaments tensioned, with a single hand of a user.

14. A ligament tensioning and gap measuring device as claimed in claim 13, wherein the handle descends from the main body.

15. A ligament tensioning and gap measuring device as claimed in claim 14, wherein the user control to initiate tensioning comprises a trigger, wherein the main body, handle, and trigger form a gun-shaped configuration.

16. A ligament tensioning and gap measuring device as claimed in claim 15, wherein the tensioning arrangement comprises a ratchet mechanism for raising the central tensioning element.

17. A ligament tensioning and gap measuring device claimed in claim 1, wherein the tensioning arrangement comprises a ratchet mechanism for raising the central tensioning element.

18. A ligament tensioning and gap measuring device as claimed in claim 1, wherein the measuring arrangement for engaging lateral and medial condyles is partially or wholly housed within the tibial base plate when in an inactive position.

19. A ligament tensioning and gap measuring device, comprising:
   a tibial base plate which, in use, engages a tibia; and
   a tensioning arrangement comprising a central element operable, in use, to engage a femur and set a gap between the tibial base plate and the femur when the femur and tibia are in extension and thereby apply tension to lateral and medial ligaments; and
   a measurement arrangement comprising:
      a lateral gap measuring element for engaging a lateral condyle, the lateral gap measuring element being movably mounted relative to the tibial base plate;
      a lateral gap measurement reader configured to measure a position of the lateral gap measuring element;
      a medial gap measuring element for engaging a medial condyle, the medial gap measuring element being movably mounted relative to the tibial base plate; and
      a medial gap measurement reader configured to measure a position of the medial gap measuring element;
   the measurement arrangement thereby operable, in use, to engage the lateral and medial condyles of a femur to independently measure a position of each condyle relative to the tibial base plate when the lateral and medial ligaments are tensioned by the central element.

* * * * *